Figure 1:
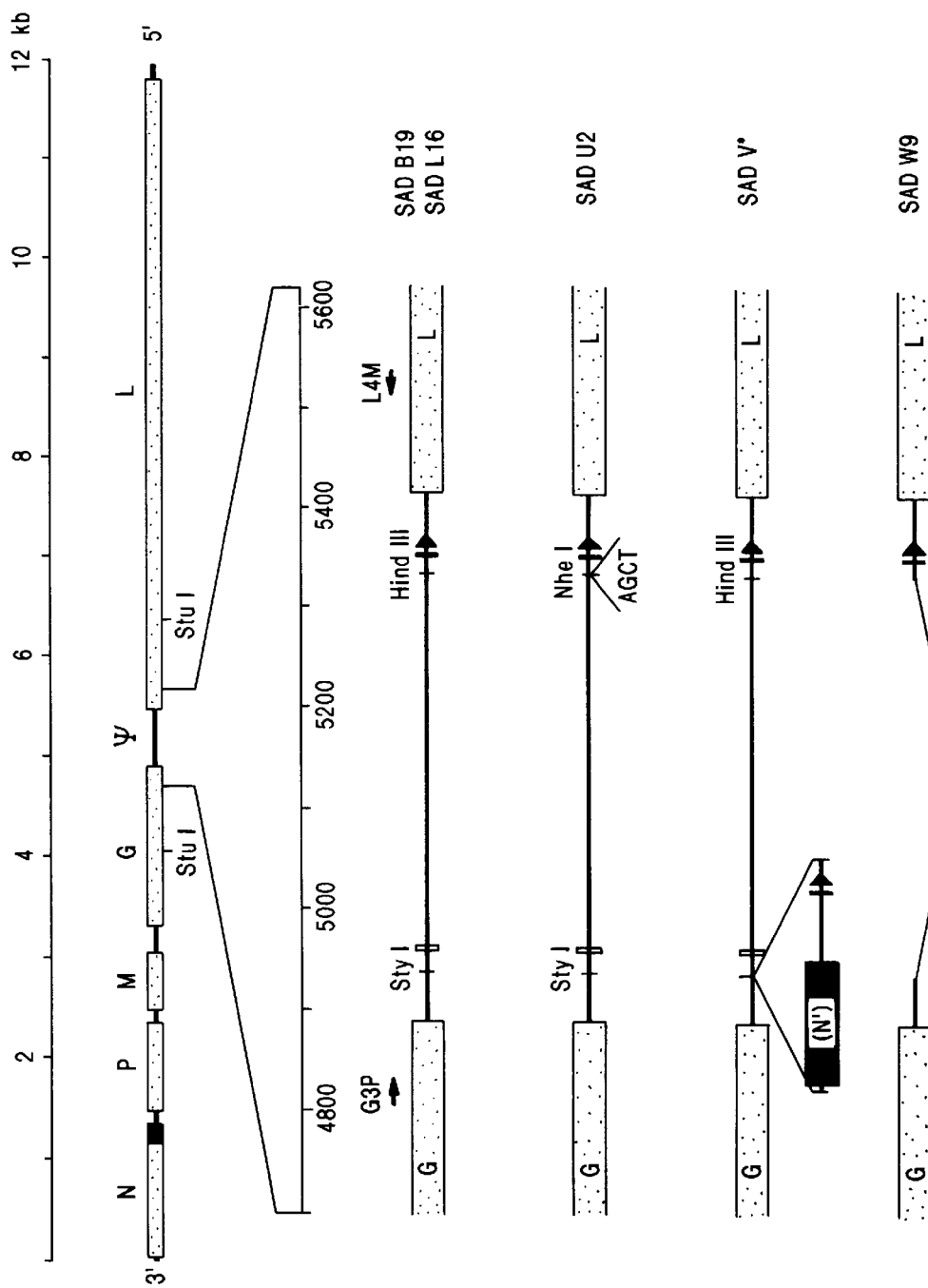

United States Patent [19]
Conzelmann

[11] Patent Number: 6,033,886
[45] Date of Patent: Mar. 7, 2000

[54] RECOMBINANT INFECTIOUS NON-SEGMENTED NEGATIVE STRAND RNA VIRUS

[76] Inventor: Karl Klaus Conzelmann, Lilienstrasse 9, D-72406 Bisingen, Germany

[21] Appl. No.: 08/808,130

[22] Filed: Feb. 28, 1997

Related U.S. Application Data

[63] Continuation of application No. 08/503,351, Jul. 18, 1995, abandoned.

[30] Foreign Application Priority Data

Jul. 18, 1994 [EP] European Pat. Off. .............. 94202089

[51] Int. Cl.[7] .......................... C12N 15/00; A61K 39/12; A61K 39/155; A61K 39/165
[52] U.S. Cl. ..................................... 435/172.3; 424/205.1; 424/211.1; 424/212.1; 424/224.1; 424/93.6; 435/235.1; 435/236; 435/172.1
[58] Field of Search ............................. 435/172.3, 235.1, 435/236, 172.1; 424/205.1, 211.1, 212.1, 224.1, 93.6

[56] References Cited

U.S. PATENT DOCUMENTS 5,166,057 11/1992 Palese et al. ........................... 435/69.1

FOREIGN PATENT DOCUMENTS

| 0440219 | 8/1991 | European Pat. Off. . |
| WO-A-9103552 | 3/1991 | WIPO . |
| WO-A-9408022 | 4/1994 | WIPO . |

OTHER PUBLICATIONS

M.J. Schnell et al., *The EMBO Journal*, 13:18:4195–4203, 1994.

D. Eschle et al., "Retraction: Infectious Measles Virus from cloned cDNA," *EMBO Journal*, 10:11:3558, 1991.

K.K. Conzelmann et al., "Rescue of Synthetic Genome Analogs of Rabies Virus by Plasmid Encoded Proteins," *J. Virol.*, 68:2:713–719, 1994.

W. Luytjes et al., "Amplification, Packaging and Expression of a Foreign gene by influenzy," *Cell* 59:6:1107–1113, 1989.

S. Li et al., "Chimeric Influenza Virus Induces Neutralising Antibodies," *J. Virol.*, 67:12:6659–6666, 1993.

A. Pattnaik et al., "Cells that Express all Five Proteins from VSV from cloned cDNAs Support Replication, Assembly and Budding of Defective Interfering Particles," *Proc. Natl. Acad. Sci. USA*, 88:1379–1383, 1991.

I. Ballart et al., Infectious Measles Virus from Cloned cDNA, *EMBO Journal*, 9:379–384, 1990.

Metsikko K and Garoff H. Oligomers of the Cytoplasmic Domain of the p62/E2 Membrane Protein of Semliki Forest Virus Bind to the Nucleocapsid In Vitro J. Virol 64 (10) 4678–4683, Oct. 1990.

Luo L and Wagner R. Transcription Inhibition Site on the M Protein of Vesicular Stomatitis Virus Located by Marker Rescue of Mutant ts023(III) with M–Gene Expression Vectors J. Virol 63 (6)2841–2843, Jun. 1989.

Conzelmann K. Genetic Manipulation of non–segmented negative–strand RNA viruses J. Gen Virol. 77(3) 381–389, 1996.

Crowe J, Bui P, London W, Davis A, Hung P, Chanock R, and Murphy B. Satisfactorily attenuated and protective mutants derived from a partially attenuated cold–passaged respiratory syncytial virus mutant by introduction of additional attenuating mutations. Vaccine 12(8): 691–699, 1994.

(List continued on next page.)

*Primary Examiner*—Jeffrey Stucker
*Assistant Examiner*—Hankyel T. Park
*Attorney, Agent, or Firm*—Michael G. Sullivan

[57] ABSTRACT

The present invention provides the generation of infectious replicating non-segmented negative-stranded RNA virus, entirely from cloned cDNA. This process offers the possibility to introduce mutations into the virus genome by means of recombinant DNA techniques.

19 Claims, 15 Drawing Sheets

OTHER PUBLICATIONS

Collins P, Mink M, and Stec, D. Rescue of synthetic analogs of respiratory syncytial virus genomic RNA and effect of truncations and mutations on the expression of a foreign reporter gene Proc. Nat'l Acad. Sci. 88 9663–9667, Nov. 1991.

Park K, Huang T, Correia F, and Krystal M. Rescue of a foreign by Sendai virus Proc. Nat'l Acad. Sci. 88 5537–5541, Jul. 1991.

Calain P, Curran J, Kolakofsky D, and Roux L. Molecular cloning of natural paramyxovirus copy–back defective interfering RNAs and their expression from DNA Virol. 191 62–71, 1992.

Pattnaik A, Ball L, LeGrone A, and Wertz G. Infectious Defective Interfering Particles of VSV from Transcripts of a cDNA Clone Cell 69:1011–1021, Jun. 1992.

Boyer J, Haenni A. Infectious transcripts and cDNA clones of RNA Viruses. Virology 198: 415–426, 1994.

FIG. 8

RV/CSFV
Leucocyte numbers (challenge day = 100%)

transmembrane domain/cytoplasmic domain

...LLSAGALTALMLIIFLMTCC/RRVNRSEPTQHNLRGTGR....  RV-G
...LVGGLRIVFAVLSIVN/RVRpRRVNRSEPTQHNLRGTGR....  HIV/RV-gp
...LVGGLRIVFAVLSIVN/RVRQGYSPLSFQTHLPIPRGPD....  HIV-gp160

FIG. 14

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

ACGCTTAACA A                              11

(2) INFORMATION FOR SEQ ID NO:2:

```
        (i) SEQUENCE CHARACTERISTICS:
              (A) LENGTH: 31 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:2:

AATTCCTGCA GTAATACGAC TCACTATAGG G                                          31

(2) INFORMATION FOR SEQ ID NO:3:

(i) SEQUENCE CHARACTERISTICS:
              (A) LENGTH: 37 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:3:

Leu Leu Ser Ala Gly Ala Leu Thr Ala Leu Leu Ile Ile Phe Leu Met
1               5                  10                  15

Thr Cys Cys Arg Arg Val Asn Arg Ser Glu Pro Thr Gln His Asn Leu
            20                  25                  30

Arg Gly Thr Gly Arg
        35

(2) INFORMATION FOR SEQ ID NO:4:

(i) SEQUENCE CHARACTERISTICS:
              (A) LENGTH: 38 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:4:

Leu Val Gly Gly Leu Arg Ile Val Phe Ala Val Leu Ser Ile Val Asn
1               5                  10                  15

Arg Val Arg Pro Arg Arg Val Asn Arg Ser Glu Pro Thr Gln His Asn
            20                  25                  30

Leu Arg Gly Thr Gly Arg
        35

(2) INFORMATION FOR SEQ ID NO:5:

(i) SEQUENCE CHARACTERISTICS:
              (A) LENGTH: 38 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:5:

Leu Val Gly Gly Leu Arg Ile Val Phe Ala Val Leu Ser Ile Val Asn
1               5                  10                  15

Arg Val Arg Gln Gly Tyr Ser Pro Leu Ser Phe Gln Thr His Leu Pro
            20                  25                  30

Ile Pro Arg Gly Pro Asp
        35
```

RECOMBINANT INFECTIOUS NON-SEGMENTED NEGATIVE STRAND RNA VIRUS

This is a continuation of application Ser. No. 08/503,351 filed Jul. 18, 1995, now abandoned.

BACKGROUND OF THE INVENTION

The present invention is concerned with a genetically manipulated infectious replicating non-segmented negative-stranded RNA virus mutant and a process for the preparation of such a mutant.

Rabies virus (RV) is an example of a non-segmented negative-stranded RNA virus of the Rhabdoviridae family. Other species belonging to this family are vesicular stomatitis virus (VSV), infectious hematopoietic necrosis virus (IHNV) viral haemorrhagic septicaemia virus (VHS, Egtved virus), bovine ephemeral fever virus (BEFV), and sonchus yellow net virus (SYNV).

Beside the family of Rhabdoviridae also viruses belonging to the Paramyxoviridae (e.g. sendai virus (SV), parainfluenza virus (PIV) type 2 and 3, Newcastle disease virus (NDV), mumps virus (MUV), measles virus (MEV) and canine distemper virus (CDV)) and Filoviridae, and several viruses not assigned to a family (e.g. Borna disease virus; BDV) have a nonsegmented negative-stranded RNA genome.

The overall genomic organisation in the non-segmented negative-stranded RNA viruses of the various families is comparable. Especially between the paramyxoviridae and the rhabdoviridae, there are only minor differences in the overall genomic organisation (Tordo et al., Seminars in Virology 3: 341–357, 1992).

RV can infect all warm-blooded animals, and in nearly all instances after establishment of symptoms the infection ends in death. Dog rabies is still important in many parts of the world: infected dogs cause most of the estimated 75,000 human rabies cases that occur each year world-wide. In many countries of Europe, and in the United States and Canada, wildlife rabies has been increasing in importance.

The clinical features of rabies are similar in most species, but there is great variation between individuals. Following the bite of a rabid animal the incubation period is usually between 14 and 90 days, but may be considerably longer, and incubation periods of over a year have been documented. Two clinical forms of the disease are recognized furious and dumb or paralytic. In the furious form, the animal becomes restless, nervous, aggressive, and often dangerous as it loses all fear of humans and bites at anything that gains its attention. The animal often cannot swallow, giving rise to the synonym for the disease, "hydrophobia". There is often excessive salivation, exaggerated responses to light and sound, and hyperesthesia. As the encephalitis progresses, fury gives way to paralysis, and the animal manifests the same clinical features as seen throughout in the dumb form of the disease. Terminally, there are often convulsive seizures, coma, and respiratory arrest, with death occurring 2–7 days after the onset of clinical signs.

Rabies virus enters the body in the bite or occasionally the scratch of a rabid animal, or when virus-loaded saliva from a rabid animal enters an open wound. Viral replication in the bite site, in muscle, is followed by invasion of peripheral nerve endings and central movement of viral genome in the cytoplasm of axons to the central nervous system. Viral entry into the spinal cord and then the brain (particularly the limbic system) is associated with clinical signs of neuronal dysfunction. Usually, at about the same time that central nervous system infection causes fury, virions are also shed from the apical end of mucus-secreting cells in the salivary glands and are delivered in high concentrations into saliva.

Throughout the course of rabies, host inflammatory and specific immune responses are only minimally stimulated; the most likely reasons for this are because the infection is noncytopathic in muscle and in nerve cells and because the infection is largely concentrated in the immunologically sequestered environment of the nervous system.

RV virions like all Rhabdoviruses are composed of two major structural components: a nucleocapsid or ribonucleoprotein (RNP) core and an envelope in the form of a bilayer membrane surrounding the RNP core. The infectious component of all Rhabdoviruses is the RNP core. The genomic RNA is of negative sense and thus cannot serve as a messenger but requires its own endogenous RNA polymerase for transcription of mRNA. The RNA genome is encapsidated by the nucleocapsid (N) protein in combination with two minor proteins, i.e. RNA-dependent RNA polymerase (L) and phosphoprotein (P) to form the RNP core. The membrane component contains two proteins: an transmembrane glycoprotein (G) and a matrix (M) protein located at the inner side of the membrane. The G-protein is responsible for cell attachment and membrane fusion in RV, and additionally is the main target for the host immune system.

During transcription, the genome directs the sequential synthesis of a short leader RNA and five monocistronic, capped and polyadenylated mRNAs. During replication, the conditional transcription stop and start signals between the cistrons are ignored by the viral polymerase. For both the transcriptase and the replicase reaction the presence of the N-protein complexed with the RNA genome as well as the L- and P-proteins are required. The gene order on the RV genome has been determined and is 3'-leader-N-P-M-G-L-5' as shown in FIG. 1. Each of the mRNAs of RV is translated immediately after transcription. Two events—occur sequentially during replication: first the production of an encapsidated complete positive strand RNA complementary to the genome, followed by the production of complete negative-stranded RNA which is also encapsidated by the N, L and P proteins. Finally, the newly assembled RNP cores associate with M-protein and G-protein during the assembly and budding process leading to the release of fully formed and infectious RV virions.

The 11.9 kb genomic RV RNA contains five open reading frames (ORFs) coding for the N, P, M, G and L proteins, in addition to the presence of a pseudogene region (ψ) between the G and L genes (FIG. 1).

Current vaccines for non-segmented negative strand RNA viruses comprise chemically inactivated virus vaccines or modified live virus vaccines comprising an attenuated virus strain the pathogenicity of which is decreased by multiple passages in cell culture. Chemically inactivated rabies vaccines are e.g.: Rabivac, Behringwerke (human), HDC, Rhone-Poulenc (human), Bayovac-LT, Bayer (vet), Madivac, Hoechst (vet), Epivax-LT, Pitman-Moore, Rabisin, Rhone-Merieux. For RV examples of such attenuated viruses are the vaccine strains SAD B19 and ERA. Inactivated vaccines generally induce only a low level of immunity, requiring repeated immunizations. Furthermore, the neutralization inducing antigenic determinants of the pathogens may become altered by the inactivation treatment, decreasing the protective potency of the vaccine.

In general, attenuated live virus vaccines are preferred because they evoke an immune response often based on both humoral and cellular reactions. However, during cell culture passaging uncontrolled mutations may be introduced into the viral genome, resulting in a population of virus particles heterogeneous with regard to virulence and immunizing properties. Over attenuation during passage in cell culture can also be a problem with these vaccines. One must achieve a delicate balance between ensuring that the vaccine is not virulent while making certain that it is still protective. In addition it is well known that such traditional attenuated live virus vaccines can revert to virulence resulting in disease outbreaks in inoculated animals and the possible spread of the pathogen to other animals.

Moreover, a problem with combined live viral vaccines is the mutual influence of the antigenic components resulting in a decrease of the potency of one or more of the constituting components.

Furthermore, with currently administered live attenuated or inactivated RV vaccines it is not possible to determine whether a specific animal is a carrier of RV field virus or whether the animal was vaccinated. Hence, it can be important to be able to discriminate between animals vaccinated with a RV vaccine and those infected with a field virus so as to be able to take appropriate measures to reduce spreading of a virulent field virus. The introduction of for example a serologically identifiable marker can be achieved by introducing a mutation in a gene encoding a (glyco-) protein of RV which normally give rise to the production of antibodies in an infected host animal.

It is desired to introduce a mutation into the RV RNA genome in a controlled manner such that for example the resulting mutant RV is attenuated or comprises a heterologous nucleic acid sequence encoding epitopes of foreign proteins, e.g. immunological marker proteins or antigens of pathogens. Recombinant DNA techniques are already widely used for this purpose with DNA viruses and positive strand RNA viruses. Examples for recombinant DNA viruses: Aujeszky virus (PRV); Adenoviruses; Vaccinia viruses. Examples for recombinant positive-strand RNA viruses: Alphaviruses (Sindbis V., Semliki forest virus: H. V. Huang, C. M. Rice, C. Xiong, S. Schlesinger (1989) RNA viruses as gene expression vectors. Virus Genes 3, 85–91). Picornaviruses (Polio virus, Hepatitis A-virus, Foot- and mouth-disease virus: J. W. Almond and K. L. Burke (1990) Poliovirus as a vector for the presentation of foreign antigens. Semin. Virol. 1, 11–20). Directed genetic manipulation of RNA virus genomes depends on the ability to produce recombinant RNAs which are accepted as a template by the particular RNA-dependent RNA polymerases. Transcripts generated by many standard DNA-dependent RNA polymerases (e.g. T7 RNA polymerase or cellular RNA polymerase II) and mimicking viral genomes are recognized by the polymerases of many positive stranded RNA viruses. This allowed recovery of infectious viruses or replicons from cDNA transcripts and the application of recombinant DNA technology to manipulate these genomes in a site specific manner. Since RNAs corresponding to the genomes of positive stranded RNA viruses may function as mRNA for translation of the viral polymerases, an infectious cycle may be initiated by introduction of the genome analogs into a cell. The template of the polymerases of negative-stranded RNA viruses, however, exclusively is the RNP complex. Moreover, and in contrast to positive stranded RNA viruses, their genomic or antigenomic RNA may not function as mRNA and thus all viral proteins involved in replication and transcription of artificial RNAs have to be provided in trans.

An appropriate system for encapsidation of genomic RNA analogs of a negative-stranded RNA viruses with a segmented genome in order to provide the appropriate template is recently disclosed by Palese, P. et al., (WO 91/03552). RNA transcripts from influenza virus genome segments were encapsidated by purified proteins in vitro which can be used to transfect cells together with a helper virus. However, it was found that this approach was not successful with RV, a virus having a non-segmented genome. Short model genomes of VSV and RV lacking the major part of the RNA genome comprising the genes encoding the viral proteins could be encapsidated and expressed by plasmid encoded proteins (Pattnaik, A. K. et al, Cell 69, 1011–1020, 1992; Conzelmann, K-K. and M. Schnell, J. Virology 68, 713–719, 1994). This approach involved the co-expression of both the genome analogs optionally comprising reporter gene inserts, and particular viral proteins from transfected plasmids in order to produce defective virus particles. Ballart et al. described a method to obtain infectious measles virus, also a non-segmented negative-stranded RNA virus, from cloned cDNA (The EMBO Journal, 9: 379–384 (1990)). A European Patent Application relating to this method was filed with the author as one of the inventors.

Both the paper and the Application were withdrawn however, since further research revealed that all supposed recombinant viruses were no recombinants at all, but mere progeny virus of the originally used vaccine strain.

Thus it must be concluded, that attempts to obtain infectious recombinant negative-stranded RNA viruses with a large, non-segmented genome which necessitates manipulation of the entire genomes, have failed until now.

SUMMARY OF THE INVENTION

The present invention provides a genetically manipulated infectious replicating non-segmented negative-stranded RNA virus mutant, obtainable by recombinant DNA techniques, comprising an insertion and/or deletion in an ORF, pseudogene region or non-coding region of the RV genome.

More specifically the invention provides non-segmented negative-stranded RNA viruses of the paramyxo- and rhabdovirus family.

As explained above, there is a large homology in genomic organisation between the non-segmented negative-stranded RNA virus families. Where the function of encoded proteins in the process of replication, assembly, cell attachment or cell fusion is comparable, these proteins will be referred to further as "analogs". It may be that the function of e.g. two proteins of one family is united in one protein in another family. This is e.g. the case with the F and HN proteins of the paramyxoviridae, that together have the same function as glycoprotein G of the Rhabdoviridae. In this case, the two proteins of the one family will be considered analogons of the one protein of the other family.

The insertion and deletion of one or more nucleic acid residues can be introduced in the RV genome by incorporating the appropriate mutations into the corresponding viral ORF, pseudogene region or non-coding region. This alteration is understood to be a change of the genetic information in the RV ORF or pseudogene of a parent RV thereby obtaining the insertion or deletion RV mutant according to the invention.

A mutation, in which one or more nucleotides are replaced by other nucleotides, a socalled substitution replacement is considered to be the result of a combined deletion and insertion action. This kind of mutation is therefore also considered to be included in the wording: deletion and(/or) insertion.

It is clear that any mutation as defined herein comprises an alteration of appropriate RV sequences such that the resulting RV mutant is still infectious and replicating, i.e. the mutant RV is capable to infect susceptible cells and its mutant RNA genome is capable of autonomously replication and transcription, i.e. no co-expression of RV N, P and L proteins is required.

It goes without saying, that also comprised in the present invention are mutant RVs capable of only one single round of infection, followed by replication (Vide infra).

The genomic organisation of different RV strains is identical. The nucleotide sequence and deduced amino acid sequence analysis of the vaccine strain SAD B19 and the virulent strain PV have been determined (Conzelmann et al., Virology 175, 485–499, 1990 and Tordo et al., Nucleic Acids Res. 14, 2671–2683, 1986; Proc. Natl. Acad. Sci U.S.A. 83, 3914–3918, 1986; Virology 165, 565–567, 1988). In Conzelmann et al., 1990 (supra) it is determined that the viral genome of the SAD B19 strain comprises 11.928 nucleotides and that the deduced amino acid sequence of the five viral proteins N, P, M, G and L are highly similar to those of the pathogenic PV strain. The location of the respective ORFs, pseudogene region and intergenic non-coding regions in RV have been determined therein: the coding region of the RV N, P, M, G and L genes correspond with positions 71–1423, 1514–2407, 2496–3104, 3317–4891, 5414–11797, respectively. The pseudogene region ($\psi$) maps at position 4961–5359, whereas the intergenic regions separating the five cistrons and which are flanked by non-coding sequences containing transcriptional start and stop/polyadenylation signals map to positions 1483–1484; 2476–2480; 3285–3289; 5360–5383. Although the numbering and the nucleotide sequence of the ORFs, pseudogene region or non-coding regions of the parent RV strain used herein to introduce a mutation is not necessarily the same as that of the SAD B19 or PV strain, the above-mentioned characterisations of these regions exactly define the localisation thereof on the genome of any RV strain.

A method to obtain an attenuated RV from a virulent parental RV strain is to introduce the insertion and/or deletion in an ORF encoding a viral protein, for example such that the activity of the viral protein for host cell attachment and membrane fusion is modified, e.g. reduced. It is known for RV that changes in the amino acid sequence of the trans-membrane glycoprotein G have significant effects on the pathogenicity of the RV. In addition, with regard to attenuation also changes in the matrix (M) protein may influence the conformation of the G protein resulting in an attenuation of the virus. Therefore, mutant RV comprising a deletion or insertion in the ORF encoding the G or M protein are particularly preferred herein.

Also comprised in the present invention are infectious replicating rabies virus mutants capable of only one single round of infection, followed by replication. The advantage thereof is explained below:

Although in general recombinant live vaccines have been proven to be safe and efficacious, there is a risk that the vaccine viruses may spread to other animals which are more susceptible to the virus.

Therefore, there is a strong reluctance on both political, ethical and partially scientific grounds, to allow the use of recombinant viruses in the field.

In particular, for risk assessment studies by regulatory authorities with respect to genetically modified vaccine viruses, especially live viruses expressing foreign genes, the aspect of possible shedding of these viruses in the environment is a very important aspect.

Thus, it can be appreciated that rabies virus vaccines which display all the advantages of live virus vaccines but which are confined to the vaccinated animals and are not shed, are highly desirable.

Such viruses can be made by e.g. mutation of the M-gene, encoding the M(atrix-)protein. The M-protein plays a main role in the assembly of the virus, whereas it additionally influences the incorporation and conformation of the glycoprotein G.

When $M^{(-)}$ mutants, lacking a functional M-protein, are grown in manipulated cells that produce the M-protein in trans, intact virus particles are made, that behave like wild-type virus as far as their infectious character towards their natural host is concerned. Once they have infected a host cell however, there is no possibility to form new infectious viruses, since they lack the genetic information to synthesize the M-protein.

Therefore, they remain contained in the host. The advantages of such viruses will be discussed below.

Therefore, in a preferred embodiment the present invention relates to an insertion and/or deletion in the open reading frame encoding the matrix protein M, such that it results in a non-functional matrix protein M, or even in the absence of matrix protein M. The $M^{(-)}$ mutant viruses with the non-functional or absent matrix protein M have to be grown in cells that provide a matrix protein M analog in trans, in order to phenotypically complement the virus.

Alternatively, such viruses can be made by e.g. mutation of the G-gene. The G-protein plays a main role early in infection, in the process of cell attachment and membrane fusion, as mentioned before.

It is possible to mutate the G-gene by insertion and/or deletion (or even by deletion of the whole G-gene) to such an extent that the resulting $G^-$ mutant virus is no longer capable of successfully infecting other cells, due to heavily impaired (or even absent) glycoprotein G. Such mutants will further be referred to as G-minus ($G^-$-) mutants.

This kind of mutations of the G-gene is therefore more severe than the mutation described before, that only lead to decreased virulence: complete $G^-$ mutants are not infectious, since they lack a functional glycoprotein G.

If such $G^-$ mutant viruses are grown in recombinant host cells complementing for the G-protein, progeny viruses are excreted that are phenotypically G-positive, but genotypically G-negative.

These viruses have an important advantage over G-positive viruses: on the one hand, they are capable of infecting non-complementing host cells, since they possess the G-protein in their membrane. In the infected cells, the $G^-$ mutant viruses replicate as wild-type viruses. This has the advantage that the whole viral genome, including heterologous genes cloned into the recombinant virus, is multiplied, and the encoded genome products will be expressed and processed as with wild-type virus.

On the other hand however, no infectious progeny virus can be made in the host, since normal host cells do not synthesize G-protein, and the mutant virus itself is genotypically G-negative.

Thus, animals infected with $G^-$ mutant virus do not shed infectious virus in the environment. This makes $G^-$ mutants (as well as the $M^{(-)}$ mutants discussed above) very safe as a basis for vaccines.

Alternatively, the $G^-$ mutants according to the invention can be complemented phenotypically by other, non-rabies-, glycoproteins known to play a role in cell attachment.

Since glycoprotein(s) protruding from the viral membrane into the environment are known to determine the cell-specificity, it therefore is possible to target the recombinant infectious rabies virus mutant to specific cells other than the natural host cells of rabies, by chosing the right complementing glycoprotein.

These glycoproteins will further be called "glycoprotein G analogs", to indicate that they are involved in cell-specific attachment, like glycoprotein G.

It should be noticed, that in some viruses, the "glycoprotein G analogs" determining the cell specificity are not glycoproteins but non-glycosylated proteins. It is clear, that these proteins are also within the scope of the invention.

Therefore, in another preferred embodiment of the present invention, the insertion and/or deletion in the open reading frame encoding the glycoprotein G is such that it results in a non-functional glycoprotein G, or even in the absence of glycoprotein G. The $G^{(-)}$ mutant viruses with the non-functional or absent glycoprotein G have to be grown in cells that provide a glycoprotein G analog in trans, in order to phenotypically complement the virus.

In an even more preferred embodiment of the present invention, the glycoprotein analog used for complementation is the rabies virus glycoprotein G itself.

Recombinant infectious rabies viruses with a glycoprotein G analog have several important advantages:
 a) they can be specifically targeted to certain cells, organs or hosts, depending on the target of the glycoprotein G analog that was chosen, This implies that e.g. specifically the respiratory tract or the digestive tract can be targeted. Thus, e.g. mucosal responses can be obtained at a predetermined site.

Alternatively, specific cells of the immune system can be targeted.
 b) they can additionally be carriers of foreign genetic information encoding epitopes from non-rabies pathogens as explained above.

Alternatively, they can be carriers of foreign genetic information encoding toxic substances.

A very important application of viruses according to the invention is obtained with viruses having both a glycoprotein G analog according to a) and foreign genetic information according to b).

Recombinant infectious rabies viruses can be obtained according to the present invention, that are targeted to a specific cell type, normally attacked by a non-rabies virus, while at the same time carrying an immunoprotective determinant of that non-rabies virus.

Such a virus induces immunity in the host against the non-rabies virus, whereas at the same time it is fully safe, due to the lack of genetic information for the glycoprotein G analog.

Another important embodiment of the present invention are viruses according to the present invention that are e.g. targeted to CD4-cells, that represent target cells of HIV, through genotypical complementation with HIV gp 120, and that facultatively encode a cytotoxic protein.

Such viruses will selectively attack CD4-cells, and once inside these the cells, they will kill them.

Alternatively, recombinant infectious rabies viruses according to the present invention can provide very safe vaccines against virulent/pathogenic viruses against which at this moment no safe live vaccines exist: a recombinant infectious rabies virus targeted against e.g. the natural target cells of Bovine Respiratory Syncytial Virus (BRSV) through complementation with BRSV glycoprotein G analog, and expressing immunoprotective epitopes of BRSV, gives a very safe vaccine against this disease.

Parainfluenza virus vaccines have so far faced the same problems as BRSV-vaccines. Therefore, recombinant infectious rabies virus with parainfluenza glycoprotein G analog and additional immunogenic epitopes of parainfluenza provides a good and safe vaccine against this disease.

Other important veterinary vaccines based on recombinant infectious rabies virus are made by introduction into the recombinant rabies virus of immunogenic determinants of
 i) the toroviruses; equine, bovine and porcine torovirus,
 ii) the coronaviruses; bovine, canine, porcine and feline coronavirus, especially the spike-proteins thereof.

Therefore, a most preferred embodiment of the present invention relates to recombinant infectious rabies virus glycoprotein $G^{(-)}$ mutants, complemented with a glycoprotein G analog, and carrying a heterologous nucleic acid sequence encoding an epitope or polypeptide of a pathogenic virus or microorganism.

Alternatively, attenuation of the RV may be obtained by altering the enzyme activity of the RV replicase or transcriptase so that the enzyme is less active, thereby resulting in the production of less infectious virions upon infection of a host animal. As the N, P and L proteins are involved in the RV polymerase activity, RV mutants having an insertion or deletion in the ORF encoding the N, P or L proteins are also part of the invention.

RV deletion and/or insertion mutants according to the invention can also be used to vaccinate a host in order to be able to discriminate (serologically) between a host to which a vaccine comprising said RV mutant is administered and a host infected with a parental RV. In this embodiment of the invention the insert in the RV insertion mutant may encode a heterologous epitope which is capable of eliciting a specific non-RV immune response in an inoculated host, or may encode a protein with enzymatic activity, such as CAT or lacZ (Conzelmann and Schnell, 1994, supra). A preferred region for the incorporation of such inserts is the RV pseudogene region. As is demonstrated in the Examples insertions and deletions can be made in this region without disrupting essential functions of RV such as those necessary for infection or replication. The RV deletion mutant may lack an epitope of a RV protein against which an immune response is normally raised by the vaccinates, in particular a RV mutant comprising a deletion in the ORF encoding the G protein is suited for this purpose. In the case of a RV insertion mutant the insertion comprises a nucleic acid sequence encoding a serological marker antigen or an epitope thereof.

In a further embodiment of the invention a RV mutant is provided which is capable of expressing one or more different heterologous epitopes or polypeptides of a specific pathogen.

Such a mutant can be used to vaccinate animals, both domestic and non-domestic animals, against wildlife rabies and said pathogen.

Vaccination with such a live vector vaccine is preferably followed by replication of the RV mutant within the inoculated host, expressing in vivo the heterologous epitope or polypeptide along with the RV polypeptides. The polypeptides expressed in the inoculated host will then elicit an immune response against both RV and the specific pathogen. If the heterologous polypeptide derived from the specific pathogen can stimulate a protective immune response, then the animal inoculated with the RV mutant according to the invention will be immune to subsequent infection by that pathogen as well as to infection by RV. Thus, a heterologous nucleic acid sequence incorporated into a suitable region of the RV genome may be continuously expressed in vivo, providing a solid, safe and longlasting immunity to the pathogen.

In particular, the present invention provides a RV vector which comprises an insertion of a nucleic acid sequence encoding an epitope or polypeptide of a specific pathogen, wherein the insertion is made in the pseudogene region.

If desired, part or whole of the pseudogene region can be deleted in the RV vector described above.

Preferably nucleic acid sequences encoding an epitope or polypeptide of canine parvovirus, canine coronavirus and classical swine fever virus (CSFV) are contemplated for incorporation into a suitable region of the RV genome.

The possibility to manipulate the non-segmented negative-stranded RNA genome of RV on the DNA level by recombinant DNA techniques was not possible until now, because no infectious replicating virus could be generated. However, a process is provided herein which allows the engineering of a mutation into a coding region or non-coding region of the viral genome on the DNA level by means of recombinant DNA techniques followed by the generating of an infectious replicating RV harbouring the mutation in its genome.

This process according to the invention comprises the steps of
a) introducing into cells expressing a RNA polymerase;
  1) one or more DNA molecules encoding the RV N, P and L proteins, and
  2) a DNA molecule comprising the RV cDNA genome and
b) isolating the viruses produced by the cells.

Normally, the cDNA of the rabies virus genome is modified by the incorporation of a mutation in the genome.

The process may however also be used to e.g. purify contaminated RV pools. In that case, the original non-mutated cDNA will be used.

In view of the fact that rescue efficiency of a model mini-genome of RV comprising heterologous inserts with plasmid encoding proteins is extremely low and moreover correlates with insert length (Conzelmann and Schnell, 1994, supra) it could not be expected that initiation of a productive infection from transfected full length genomic RNA could be achieved by co-transfection with plasmids encoding the RV N, P and L proteins. This is the more so as large amounts of positive sense N, P and L specific RNAs are produced from the transfected protein encoding plasmids which were expected to hybridize with simultaneously expressed negative-stranded genomic RNA transcripts. Possible hybridization, however, which could affect more than half of the genome was suspected to interfere with the crucial encapsidation step. In addition, translation of N, P and L mRNA might be affected. Indeed it was found that with the standard transfection protocol no infectious viruses could be obtained. However, as demonstrated in the examples the application of an alternative transfection protocol in combination with the use of a RV cDNA genome generating positive stranded antigenomic RNA transcripts, gave rise to a replicating genetically engineered RV.

The above-mentioned process allows the in vitro incorporation of a mutation in the genome of a parental RV by means of recombinant DNA techniques followed by the generation of an infectious replicating RV mutant harbouring said mutation. The mutation includes but is not limited to an insertion, deletion or substitution of nucleic acid residues into an ORF encoding a RV protein, a non-coding region e.g. the pseudogene region, or a transcriptional signal sequence of RV parental genome.

The engineering of a mutation in a non-coding intergenic region may influence the transcription of a specific viral gene such that the transcription of the mRNA and the subsequent translation of the protein, either an envelope protein, such as the M and G protein or a protein involved in polymerase activity, such as the N, P or L protein, is reduced resulting in a virus mutant featuring attenuated characteristics because the mutant's capability of producing (infectious) progeny virus is reduced. In particular the substitution of one or more nucleic acid residues in this intergenic region and/or transcriptional signal sequences can influence efficiency of transcription.

Furthermore, the substitution of one or more nucleic acid residues in a region of the genome of a virulent RV which is involved with virulence, such as the ORF encoding the G protein, by the application of the process described herein is part of the invention.

Such a mutation may result in the exchange of a single amino acid in the G protein of a virulent RV strain resulting in a (partial) loss of pathogenicity, e.g. replacement of Arg (333) with Ile, Glu or Gln, or Leu (132) by Phe, or Trp.

In the process according to the invention the DNA molecule containing the RV genetic information preferably comprises a plasmid provided with appropriate transcription initiator and terminator sequences recognizable by a polymerase co-expressed by the transfected host cells.

A preferred process according to the invention comprises the use of host cells transfected with RV DNA, said cells being able to express bacteriophage T7 DNA-dependent RNA polymerase, expressed for example cytoplasmically from vaccinia virus recombinant. In this case the plasmids containing RV DNA are provided with the T7 promoter and terminator sequences (Conzelmann and Schnell, 1994, supra).

For the preparation of a live vaccine the recombinant RV mutant according to the present invention can be grown on a cell culture derived for example from BHK, or human diploid cells. The viruses thus grown can be harvested by collecting the tissue cell culture fluids and/or cells. The live vaccine may be prepared in the form of a suspension or may be lyophilized.

In addition to an immunogenically effective amount of the recombinant RV the vaccine may contain a pharmaceutically acceptable carrier or diluent.

Examples of pharmaceutically acceptable carriers or diluents useful in the present invention include stabilizers such as SPGA, carbohydrates (e.g. sorbitol, mannitol, starch, sucrose, glucose, dextran), proteins such as bovine serum or skimmed milk and buffers (e.g. phosphate buffer).

Optionally, one or more compounds having adjuvant activity may be added to the vaccine. Suitable adjuvants are for example aluminium hydroxide, phosphate or oxide, oil-emulsions (e.g. of Bayol F$^{(R)}$ or Marcol 52$^{(R)}$, saponins or vitamin-E solubilisate.

The useful dosage to be administered will vary depending on the type of mammal to be vaccinated, the age, weight and mode of administration.

The dosage may vary between wide ranges: $10^2$ to $10^7$ pfu/animal would e.g. be suitable doses.

A specific dosage can be for example about $10^6$ pfu/animal.

A RV mutant according to the invention can also be used to prepare an inactivated vaccine.

For administration to animals, the RV mutant according to the present invention can be given inter alia orally, intranasally, intradermally, subcutaneously or intramuscularly.

The RV vaccine according to the invention can be administered to dogs but also to the main vectors, i.e. raccoons, skunks and foxes. Furthermore, also vaccination of wild boars with a live RV vector capable of expressing a heterologous gene of a porcine pathogen such as classical swine fever virus, is contemplated.

EXAMPLE 1

Figure 2:
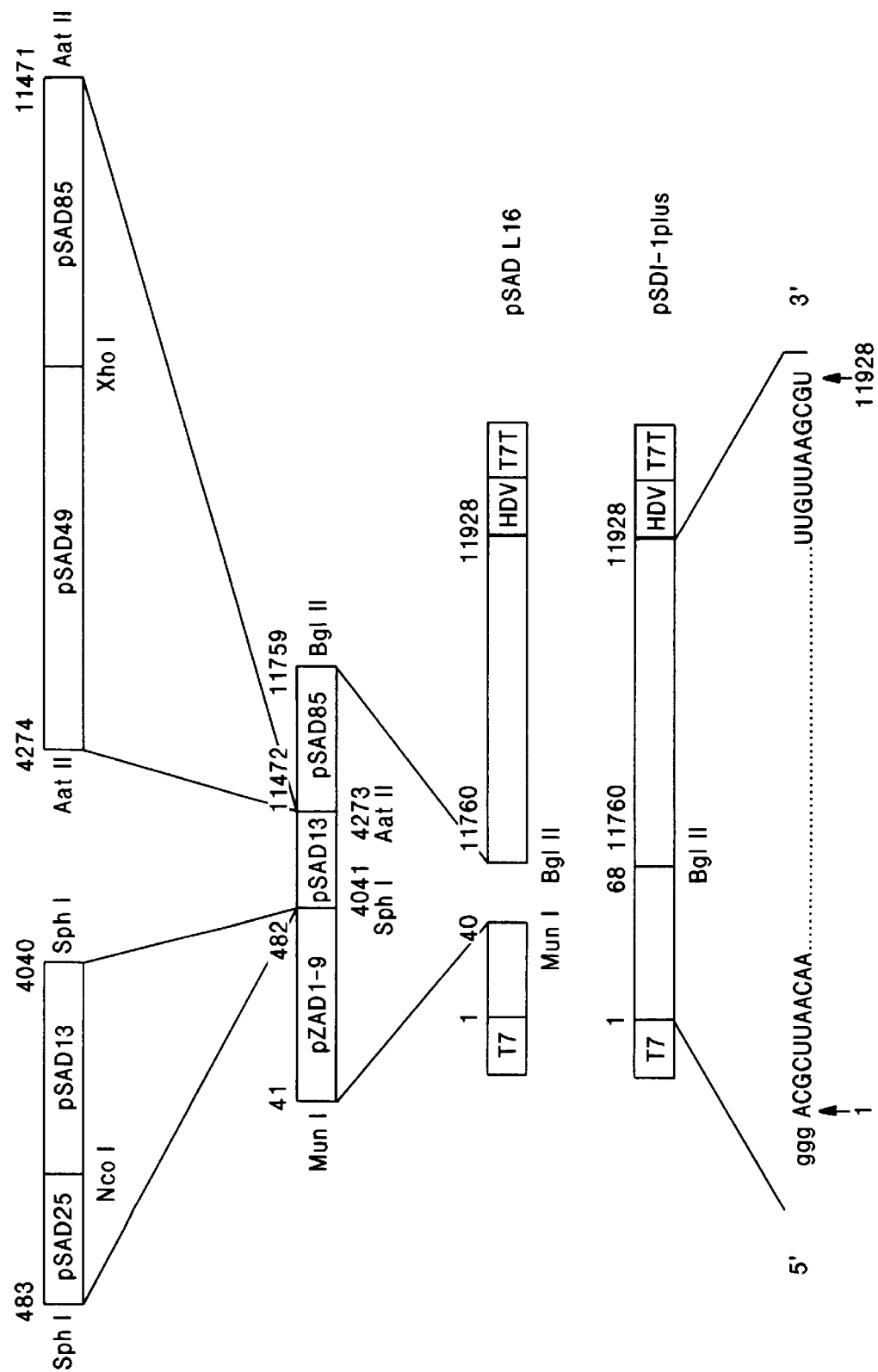

Preparation of Infectious Replicating RV Virions
Construction of Full Length RV cDNA (FIG. 2).

The cloning of cDNA spanning the entire genome of RV strain SAD B19 was described previously (Conzelmann et al., 1990, supra; GenBank accession number M31046). The numbering of RV nucleotides and amino acids used herein corresponds to that of Conzelmann et al., 1990 (supra). As basis for the assembly of a SAD B19 full length DNA clone the RV mini-genome sequence contained in the transcription plasmid pSDI-1 (Conzelmann and Schnell, 1994, supra) was used (FIG. 2). pSDI-1 contains the SAD B19 genomic 3' and 5' ends (SAD B19 nucleotides 1–68 and 11760–11928, respectively) inserted between a T7 RNA polymerase promoter and the hepatitis delta virus (HDV) antigenome ribozyme sequence. In order to generate a plasmid to produce positive stranded SDI-1 transcripts (pSDI-1plus) the RV sequences contained in pSDI-1 were first amplified by PCR using an 11 base primer (5'-ACGCTTAACAA-3') (SEQ ID NO:1) which due to the complementarity of RV genome ends corresponds to the 5' termini of both positive and negative sense viral RNAs. After subsequent partial ligation of a synthetic EcoRI/blunt adaptor (T7/3) containing a T7 promoter sequence followed by three G residues (underlined) (5'-AATTCCTGCAGTAATACGACTCACTATAGGG-3') (SEQ ID NO:2) to the amplified RV sequence, the ligation products were cloned in the EcoRI/SmaI sites of pX8dT. This plasmid is a derivative of pBluescriptII (Stratagene) from which a BssHII/ClaI fragment of the multiple cloning site containing the original T7 promoter was deleted. It contains the 84 base HDV antigenomic ribozyme sequence in the SmaI site followed immediately by a T7 transcription terminator sequence cloned in the BamHI site. Constructs that contained a T7 promotor upstream of the plus sense RV sequence were identified by restriction analysis and sequencing. The MunI-BglII fragment of pSDI-1 (SAD B19 nucleotides 40–68) was then replaced with a 1 kb MunI/BglII cDNA construct assembled in pBluescriptII from three fragments of different SAD B19 cDNA clones (MunI-SphI (SAD B19 nucleotides 40–482 from pZAD1–9); SphI-AatII (4041–4273 from pSAD13), and AatII-BglII (11472–11759 from pSAD85)) resulting in pSDI-1170. By insertion of a SphI fragment assembled from the clones pSAD25 and pSAD13 via NcoI (SAD B19 nucleotides 482–4041) and an AatII fragment assembled from clones pSAD 49 and pSAD85 via XhoI (SAD B19 nucleotides 4273–11472) into the unique SphI and AatII sites of pSDI-1170, the final basic full length clone pSAD L16 was completed. Using the circular plasmid, in vitro transcriptions were performed and the products analyzed on denaturing agarose gels. The presence of RNA transcripts co-migrating with 12 kb RV genomic RNA indicated that full length antigenome RNA is transcribed by T7 polymerase.

Recovery of Infectious Recombinant RV

The co-transfection of plasmid pSAD L16 and plasmids encoding RV proteins N, P and L was carried out as described in Conzelmann and Schnell, 1994 (supra).

Transfection experiments were carried out as described previously. BHK-21, clone BSR cells were grown overnight in 3.2 cm-diameter dishes in Eagle's medium supplemented with 10% calf serum to 80% confluence, and infected at a m.o.i. of 5 with the recombinant vaccinia virus vTF7-3 (Fours et al., Proc. Natl. Acad. Sci U.S.A. 83, 8122–8126, 1986). One hour post-transfection cells were washed twice with culture medium lacking calf serum and transfected with a plasmid mixture containing 5 μg pT7T-N, 2.5 μg pT7T-P, and 2.5 μg pT7T-L and with 2 μg of pSAD-L16 plasmid by using the mammalian transfection kit (Stratagene; CaPO$_4$ protocol) according to the suppliers instructions. The precipitate was removed 4 h posttransfection and cells were washed and incubated in Eagle's medium containing 10% calf serum. Possible encapsidation of pSAD-L16 derived T7 RNA polymerase transcripts and the resulting expression of RV proteins from the nucleocapsids was checked by indirect fluorescence. A monoclonal antibody directed against RV G protein, which could only be expressed from the recombinant RV genome, was used to screen the cultures. One day after transfection stained cells were present, demonstrating expression of genes from the RV genome. However, only single positive cells were observed in a series of 20 transfection experiments. No fluorescent cell foci indicating the presence of infectious virus were obtained in these experiments. In addition, from cell cultures which were inoculated with the entire supernatant from the transfected cells no infectious virus could be recovered two days later. Therefore, in order to isolate a presumed very low number of infectious virus generated in transfected cells, the experimental procedure was modified. For isolation of transfectant viruses cells and supernatants were harvested 2 days post transfection. Cells were suspended in the supernatant by scratching with a rubber policeman. The suspension was submitted to three cycles of freezing and thawing (−70° C./37° C., 5 min each). Cellular debris and the excess of vaccinia virus which forms aggregates under these conditions was pelleted by 10 min of centrifugation at 10.000 g in a microfuge. The entire supernatant was used to inoculate a culture dish with a confluent monolayer of cells. After incubation for 2 h, the supernatant was replaced by 2 ml of fresh culture medium. A cythopathogenic effect (cpe) caused by vaccinia virus was observed one to two days post infection. In average only ten plaques were observed after centrifugation at 10.000 g. RV infection of cells, which does not result in detectable cpe was demonstrated two days post infection by direct immunofluorescence staining of the entire monolayer with an anti-N conjugate (Centocore). In two out of 20 experiments fluorescent foci were observed and the respective supernatants contained infectious RV (SAD L16) which was assumed to represent transfectant virus generated from cDNA transcripts.

Half of the supernatants from the cultures in which foci were observed, was used for the second passage after centrifugation at 10.000 g. For further passaging (2 days each) decreasing aliquots of supernatants were used according to the degree of RV infection. To get completely rid of Vaccinia virus, supernatants from cultures approaching infection of all cells (third passage) were centrifuged two times for 10 min at 14.000 g in a microfuge. The final supernatant was then filtered using a sterile MILLEX-VV 0.1 μm filter unit (Millipore Products, Bedford, Mass. 01730) and then used to produce high titre stocks of recombinant RVs.

The latter transfection and isolation protocol was used in the subsequent Examples.

EXAMPLE 2

Insertion of an Oligonucleotide in the RV Pseudogene Region

Manipulations of the ψ were carried out in the sub-clone pPsiX8, containing a 2.8 kb XhoI-ScaI fragment of pSAD L16 representing SAD B19 nucleotides 3823 to 6668. The StuI fragments of the modified pPsiX8 plasmids were then isolated and used to replace the corresponding fragment (SAD B19 position 4014 to 6364) of the full length clone pSAD L16 (FIG. 1). Insertion of 4 nucleotides into the ψ and generation of a novel NheI site was achieved by digestion of pPsiX8 with Hind III, fill in of the extensions with Klenow enzyme and religation. The final full length clone pSAD U2 is distinguished from SAD L16 by the duplication of nucleotides 5338 to 5341.

Figure 3:
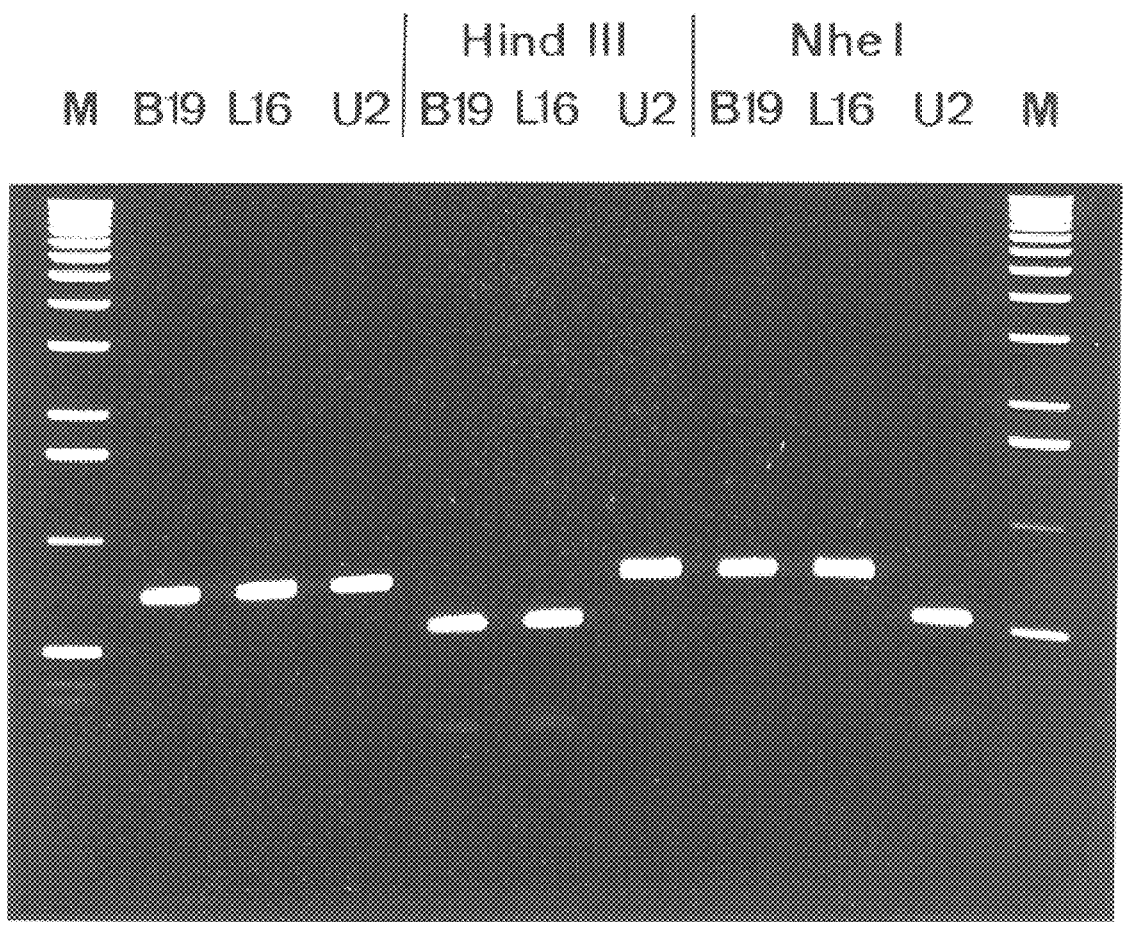

The generation of infectious viruses was demonstrated after transfer of extracts from transfected cells together with supernatant to fresh cells. In each of the series focus formation was observed in one experiment. The transfectant viruses (clones SAD U2-13 and SAD U2-32) were passaged by transfer of supernatants to fresh cells two further times resulting in almost 100% infection of the cells. To demonstrate the insertion in the SAD U2 virus genome, total RNA was isolated from cells infected with SAD U2-13 and reverse transcriptase-PCR (RT-PCR) of the ψ was performed. With the primers G3P and L4M (FIG. 1), which are specific for the G and L genes, respectively, DNA fragments of approximately 730 bp were obtained from the genomes of transfectant viruses SAD U2 and SAD L16 and of standard RV SAD B19. However, subsequent digestion with HindIII was only observed for the PCR DNA obtained from SAD B19 and SAD L16, but not for that from SAD U2. Conversely, only SAD U2 derived DNA was digested with NheI, giving rise to two fragments of approximately 530 and 200 bp, respectively (FIG. 3). Direct RT sequencing of genomic RNA of transfectant virus SAD U2 further confirmed the presence of the expected insertion of 4 residues at the predicted site, while the rest of the determined sequence corresponded to that of the original SAD B19 genome. Thus, it was clear that SAD U2 virus represented a transfectant virus whose genome originated from engineered cDNA.

The introduction of four additional nucleotides close to the end of the RV ψ did not affect viability of the transfectant virus SAD U2, nor did it interfere with correct transcription termination of the G mRNA.

EXAMPLE 3
Alteration of RV Transcription by an Insertion or Deletion Between G and L Coding Region By double digest with StyI and HindIII, Klenow fill in and religation, 396 bases (SAD B19 nucleotides 4942 to 5337) were deleted, the final construct was pSAD W9. For the construction of pSAD V*, a 180 bp BglII-AsuII fragment including the SAD B19 N/P cistron border region was isolated from pSAD13 (Conzelmann et al., 1990, supra). The fragment contained 97 nucleotides of the N coding region, the entire 3' non-coding region and the N/P cistron border consisting of the N transcriptional stop/polyadenylation signal, the intergenic region, and the first 16 nucleotides of the P cistron including the transcriptional start signal. The cDNA fragment was first sub-cloned into the EcoRI site of pBluescript after fill-in of 3' recessive ends with Klenow enzyme (pNigP-180). After excision with HindIII/XbaI from pNigP and blunt end generation the obtained 230 bp fragment which contained the RV insert flanked by 16 and 34 bp of vector derived sequences, respectively, was cloned into the filled-in StyI of pPsiX8. The final full length construct (pSAD V*) thus possessed a 234 bp insertion compared to pSAD L16.

Figure 4:
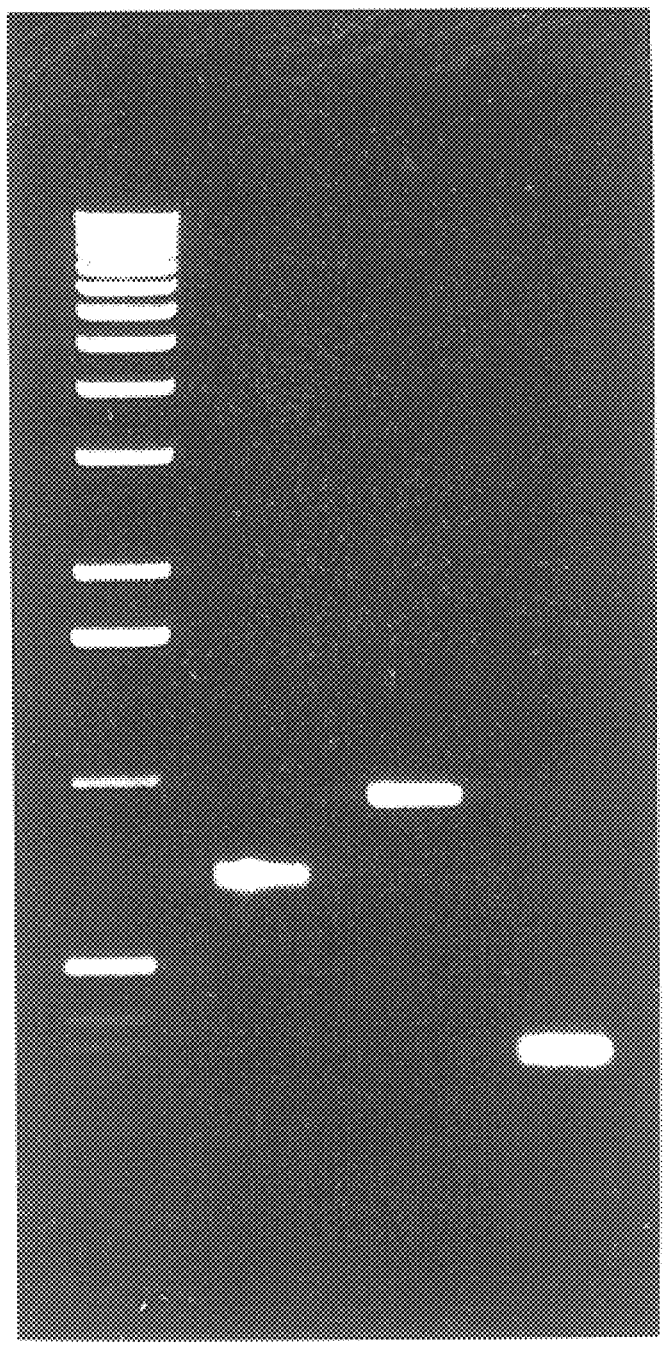

As before, pSAD V* and pSAD W9 were used to transfect twenty culture dishes each. In three cultures transfected with SAD V* and in one with SAD W9, rescue was indicated by subsequent isolation of viable virus. After five successive passages RNA from infected cells and supernatant was isolated and analyzed by RT-PCR using the same primers as in the previous experiments. In comparison to standard SAD B19 virus, an enlarged DNA fragment of approximately 0.9 kb resulted from RNA of cells infected with SAD V* thus showing that additional sequences were present in the ψ region of this transfectant virus (FIG. 4). In contrast, from RNA of cells infected with SAD W9, a DNA fragment of only 0.3 kb was obtained; this size was expected according to the deletion made in the cDNA genome copy. Sequencing of PCR products confirmed further that the original engineered cDNA sequences were rescued into the genomes of SAD V* and SAD W9 transfectant viruses. Accordingly, neither the presence of additional sequences, including 50 vector derived nucleotides, between the G open reading frame and the ψ nor the deletion of the entire ψ did interfere with the infectivity and propagation of transfectant rabies viruses. The alterations engineered into the genomes of SAD V* and SAD W9 were designed in a way to result in phenotypical changes in the transcription pattern and it was investigated whether this affected the growth characteristics of the respective transfectant viruses. However, propagation in cell culture as well as final titers of infectious SAD V* and SAD W9 viruses were similar to those of standard SAD B19 RV. Three days after infection of cells with an m.o.i. of 0.01, titers of $10^8$ focus forming units (ffu) were reached in the supernatants for SAD B19, SAD V* and SAD W9 demonstrating that the RV ψ is not essential for propagation in cell culture.

Using a ψ specific probe, no hybridization was detected with RNA from cells infected with the ψ-deleted SAD W9 virus. While the genomic RNAs of the other viruses and the G mRNAs of SAD B19 and SAD L16 were recognized by this probe, the SAD V* G mRNA did not react. In contrast, a faint band of RNA appeared that corresponded in size to the novel extra ψ-mRNA that was predicted by the presence of the extra P gene transcriptional start signal preceding the SAD V* ψ sequences. In contrast to naturally occurring RV, the transfectant virus SAD V* represents a RV whose genome is composed of six functional cistrons.

EXAMPLE 4
Expression of a Foreign Protein-Encoding Gene from Recombinant RV

The 230 bp cDNA fragment containing the N/P cistron border flanked by multiple restriction sites described in example 3 was introduced into the BstXI site of the pseudogene region of the full length cDNA pSAD L16 (SAD B19 position 4995) after generation of blunt ends with Klenow enzyme. The resulting cDNA pSAD V was used as a basis for introduction of the bacterial chloramphenicol-acetyltransferase (CAT) gene. To obtain pSAD XCAT, a 0.8 kb DNA fragment of pCM7 (Pharmacia) containing the entire CAT coding region was cloned into the AsuII site of pSAD V contained in the N/P cistron border upstream of the pseudogene sequence. For construction of pSAD VCAT, the cDNA between the AsuII site and the HindIII site located close to the end of the pseudogene sequence (SAD B19 position 5337) was deleted and replaced with the CAT-encoding HindIII-DNA from pCM7 after blunt end generation with Klenow enzyme. Accordingly, transcription of the recombinant RV SAD XCAT should give rise to a CAT mRNA possessing the pseudogene sequence as a nontranslated 3' region, whereas SAD VCAT should transcribe a CAT mRNA lacking the pseudogene sequence.

Figure 5:
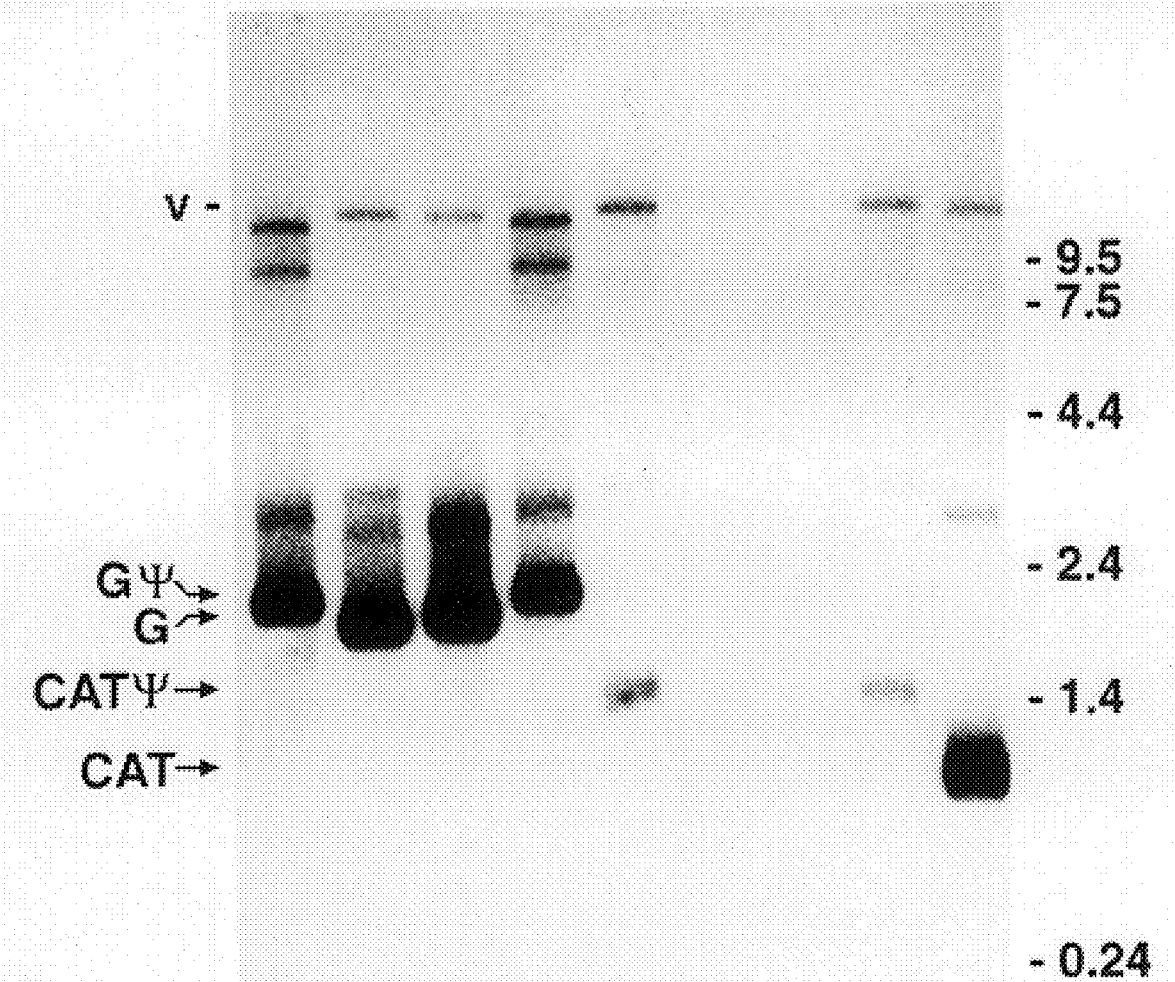
Figure 6:
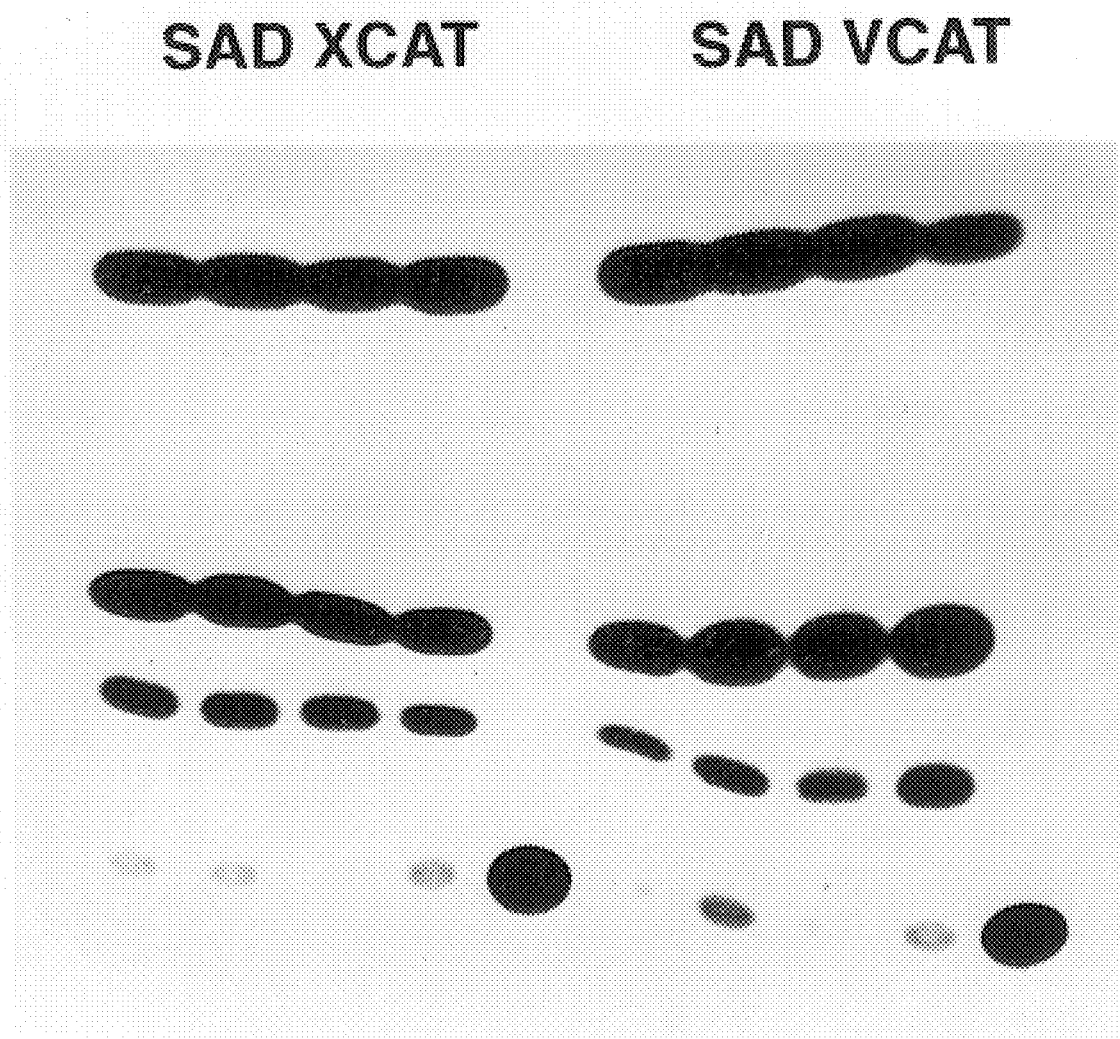

Recombinant rabies viruses were rescued after transfection of plasmids encoding RV N, P, and L proteins and pSAD-XCAT, and pSAD-VCAT, respectively, as described in Example 1. After removal of vaccinia virus, the transcription pattern of the recombinant RVs were analysed by northern hybridization. Both viruses transcribed CAT mRNAs of the expected size and composition (FIG. 5). The expression of CAT enzyme activity was determined in cells infected with the two viruses, respectively, by standard CAT assays (Conzelmann and Schnell, 1994, supra). Both were found to express CAT efficiently. Successive passages in cell culture cells showed that the introduced foreign sequences are genetically stable. Even after 40 passages both viruses expressed CAT efficiently (FIG. 6). Additional experiments were performed in order to examine expression and behaviour of the recombinant viruses in infected animals. Six week old mice (five each) were injected intracerebrally with $10^4$ ffu of SAD VCAT, SAD XCAT, and standard sequence RV SAD L16, respectively. Seven days after infection all animals showed typical rabies symptoms and died from rabies within the following week. CAT activity was demonstrated in brains of mice infected with SAD VCAT and SAD XCAT, respectively. Both viruses could be reisolated from mouse brains and expressed CAT cell culture. Thus, a foreign gene can be introduced into the genome of infectious RV and be expressed stably and as well may serve as a marker to differentiate recombinant viruses.

Figure 7A:
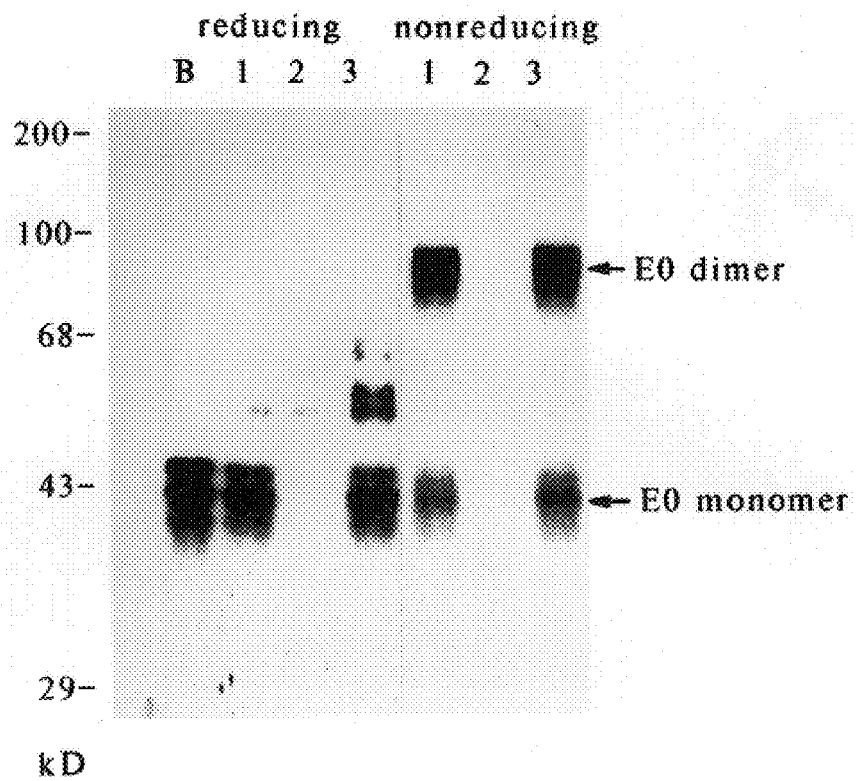
Figure 7B:
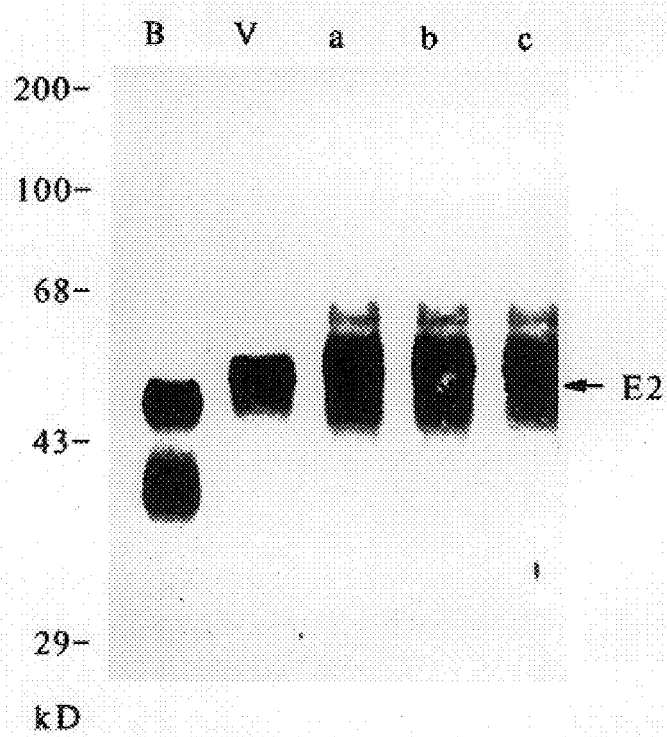

EXAMPLE 5
Expression of a Heterologous Viral Antigen from Recombinant RV and Induction of an Immune Response Against RV and the Heterologous Virus The genome of classical swine fever virus (CSFV) encodes three structural glycoproteins (E0, E1 and E2). In CSFV infected animals neutralizing antibodies are directed against E2, whereas E0 induces a cellular immune response, cDNA encompassing the coding region of the E2 protein and the E0 protein of CSFV strain Alfort respectively. were used to replace the pseudogene region between the AsuII and HindIII sites of pSAD V as described in Example 4. Recombinant viruses (SAD-VE0 and SAD-VE2, respectively) were recovered from transfection experiments as detailed in Example 1. In infected cells the viruses expressed CSFV E0 protein, and CSFV E2 protein, respectively (FIG. 7).

Figure 8:
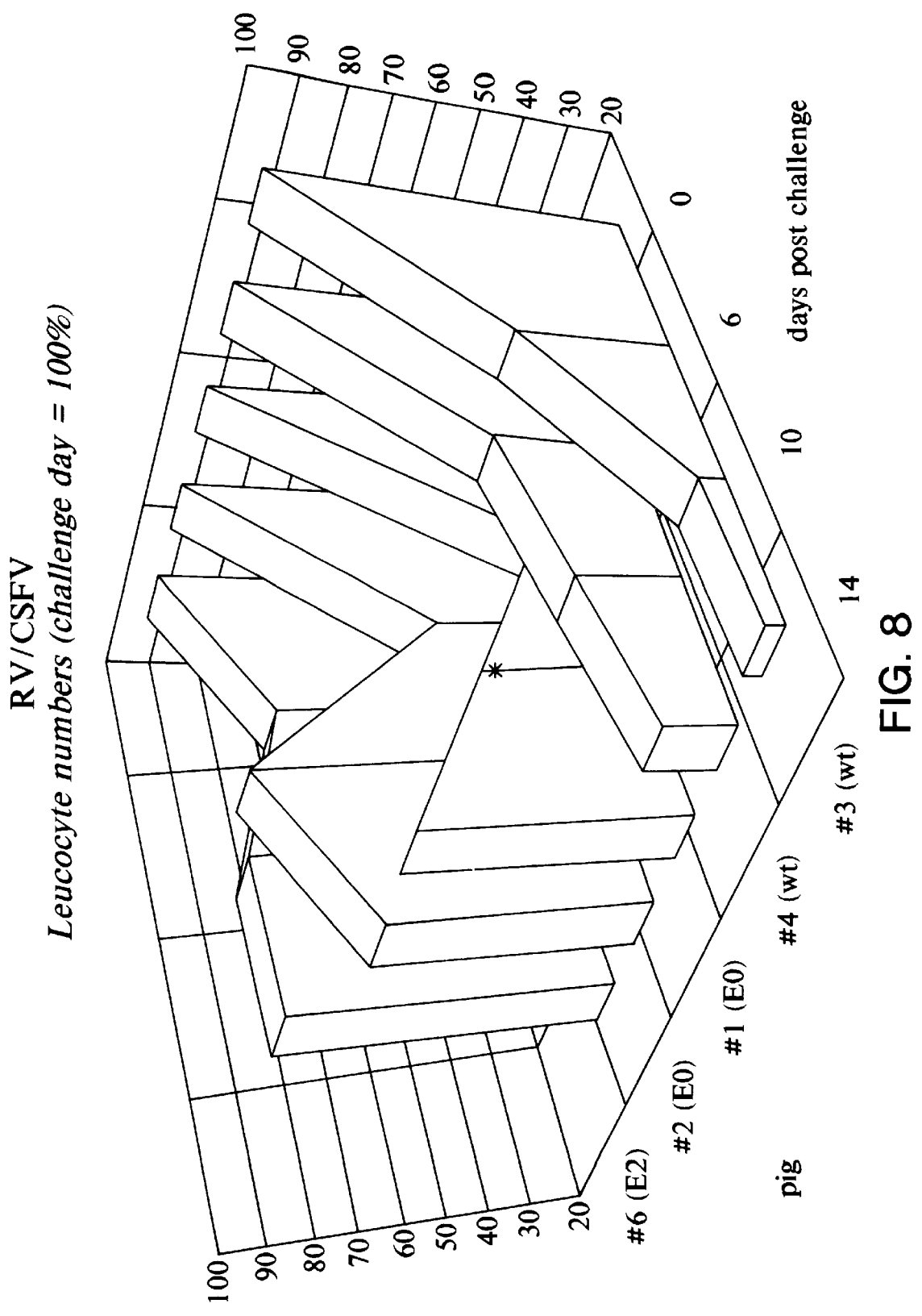
Figure 9A:
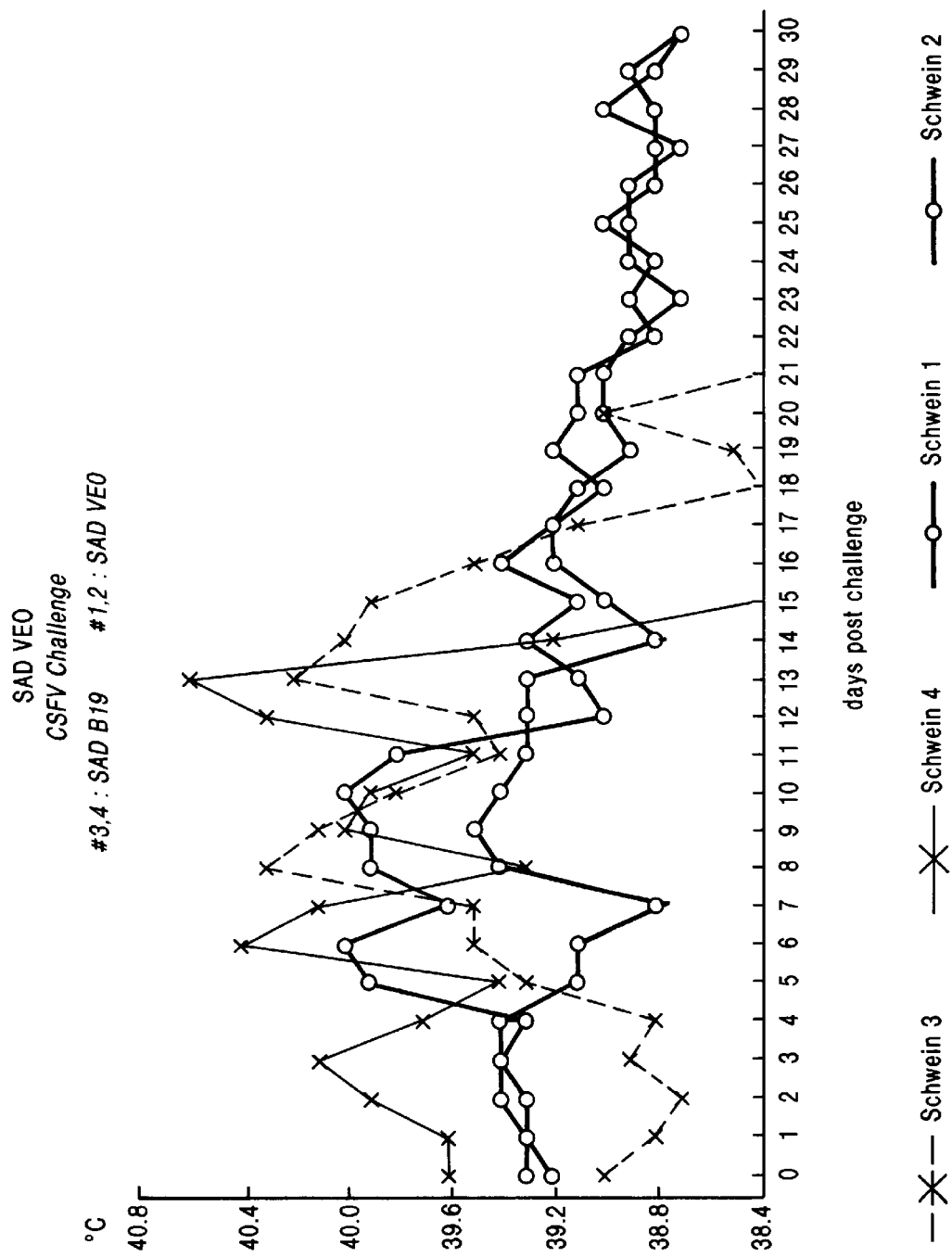
Figure 9B:
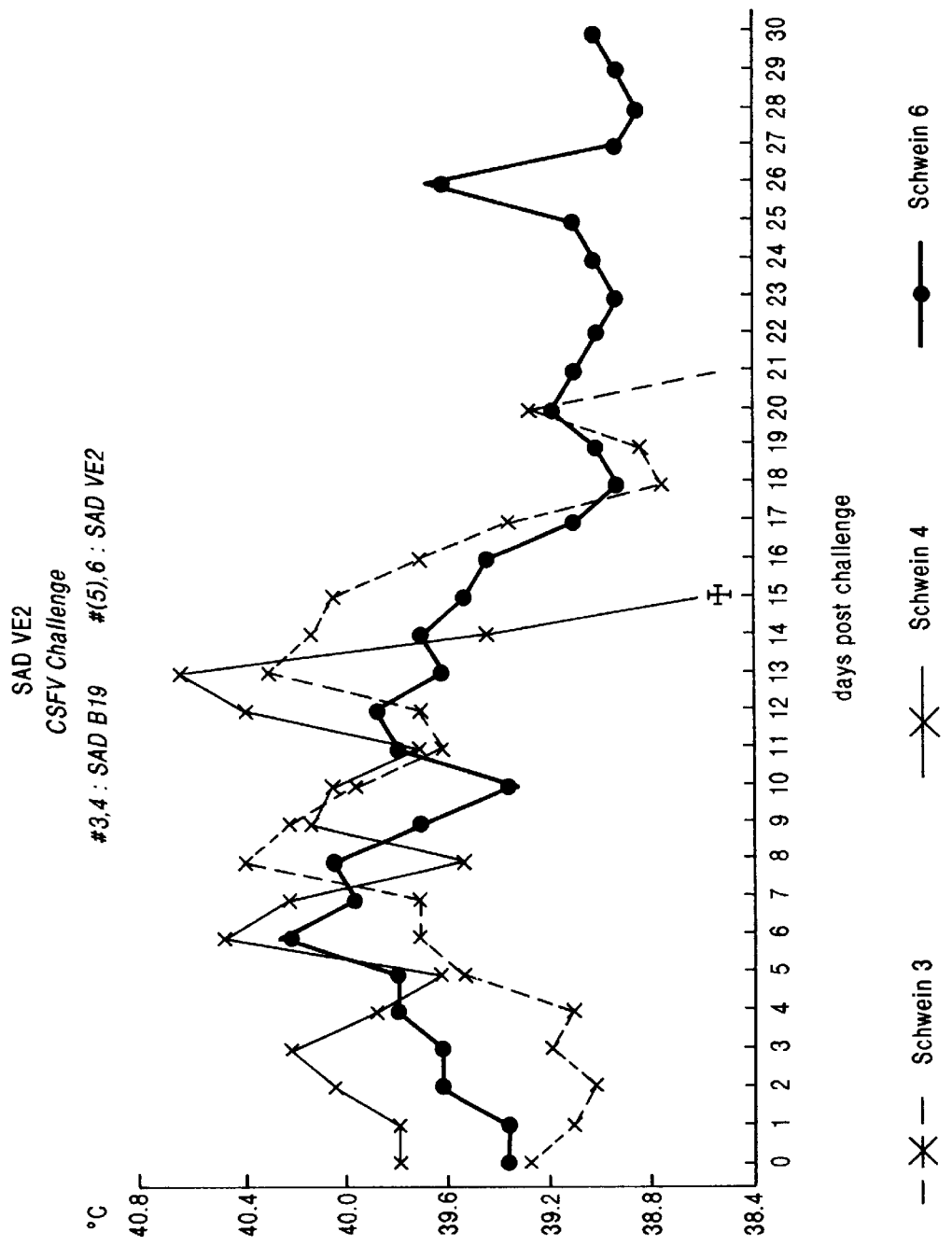

The recombinant viruses SAD VE0 and SAD VE2 were used to immunize pigs by the oral route. Standard fox baits usually being used for oral immunization of foxes with the attenuated RV SAD B19 strain were loaded with $10^7$ pfu of SAD-VE0, SAD-VE2 and SAD B19, respectively. Two baits of each preparation were fed to two pigs each (pig #1 and #2: SAD VE0, #3 and #4, SAD B19, #5 and #6, SAD VE2). Four weeks after immunization, the presence of neutralizing antibodies against RV and CSFV as analysed. With the exception of #5, all pigs possessed RV neutralizing antibodies (titre >250) confirming uptake of the vaccine baits. Pig 5 was therefore not further considered. Pig #6 developed CSFV neutralizing antibodies at a titre of >16. As expected, pigs #1 to 4 did not develop CSFV neutralizing antibodies. An intranasal challenge with $10^7$ pfu of CSFV strain Alfort was performed 5 weeks after immunization. Leucocyte numbers of pigs and body temperature were monitored after the challenge and shown in FIGS. 8 and 9, respectively. All pigs developed fever, but pigs #1 and #2 as well as #6 recovered more quickly. The control animal #4 died 15 days post challenge with typical CSFV symptoms, the control #3 was killed on day 21. The presence of CSFV neutralizing antibodies in the fig fed with SAD VE2 and the partial protection of the pigs that received either SAD VE0 or SAD VE2 demonstrate that both humoral and cellular immune responses against two heterologous viruses may be induced by recombinant RV live vaccines after application by the oral route.

EXAMPLE 6
Generation of an Attenuated RV by Introduction of a Mutation into G Gene Sequences In order to generate a virus propagating less efficiently than the standard virus SAD B19, a recombinant was prepared that possesses a mutated G protein.

For this purpose, the sequence encoding the last 46 amino acids of the G protein were deleted. First, the G protein coding plasmid, pT7T-G (Conzelmann and Schnell, 1994, supra) was digested with AflIII (position 4752 of the SAD B19 sequence) and EcoRV (the latter site is present in the multiple cloning site of the plasmid) and blunt ends were generated by Klenow enzyme. Ligation of the resulting AflIII and EcoRV ends resulted in the generation of a translation termination codon at the former AflIII sequence. A 0.3 kb DNA PpuMI-SmaI fragment containing the modified region was used to replace the authentic PpuMI-BstXI fragment 4469–4995 of pSAD L16. This manipulation resulted in the deletion of SAD B19 nucleotides 4753–4995 encoding the carboxyterminal 46 aa of the G protein cytoplasmic tail and part of the pseudogene sequence. A further result is the introduction of 18 vector-derived nucleotides immediately downstream of the new G translation termination codon.

Figure 10A:
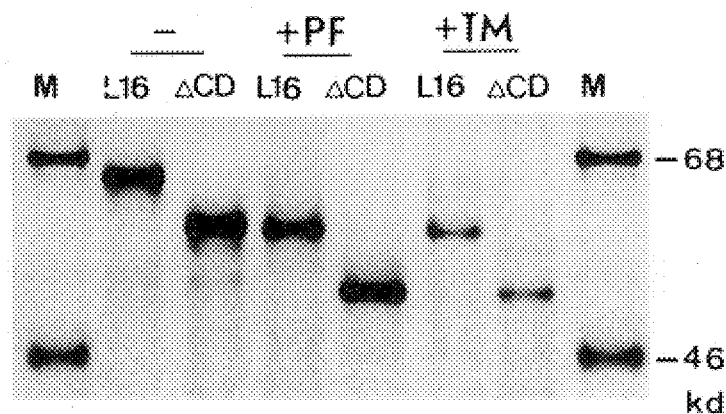
Figure 10B:
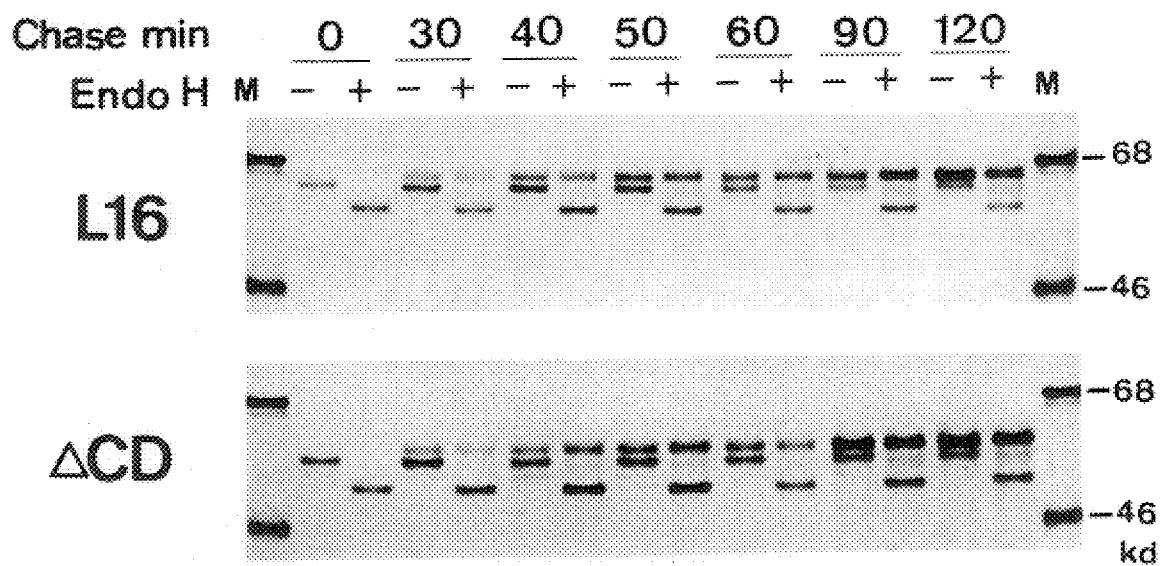
Figure 11A:
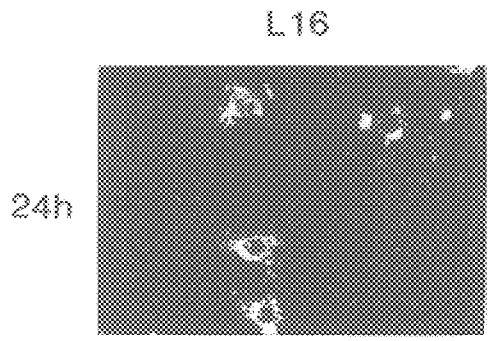
Figure 11D:
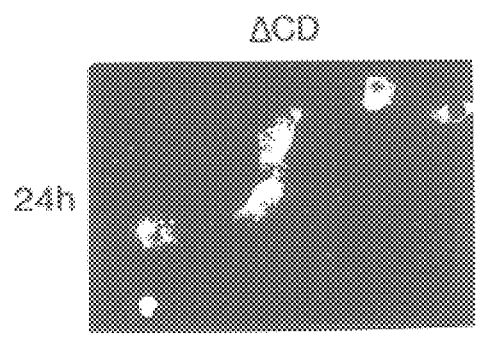
Figure 11B:
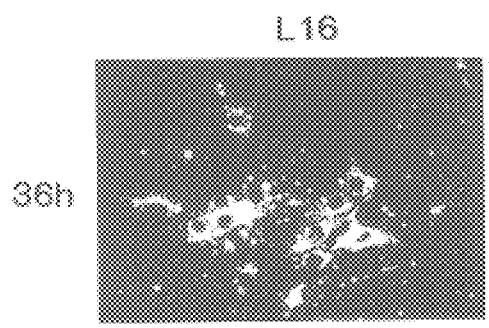
Figure 11E:
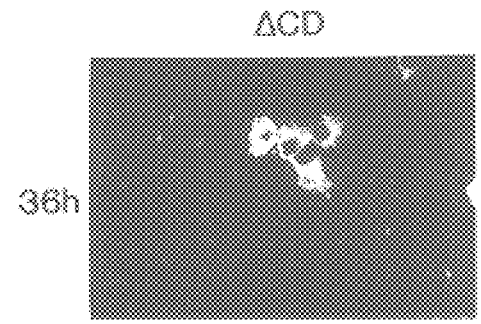
Figure 11C:
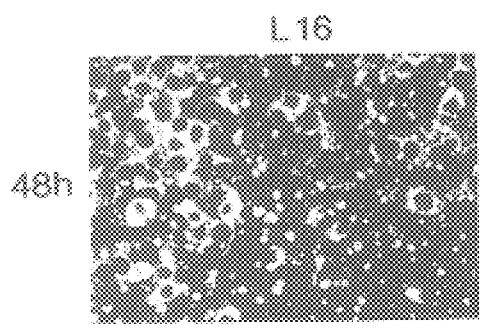
Figure 11F:
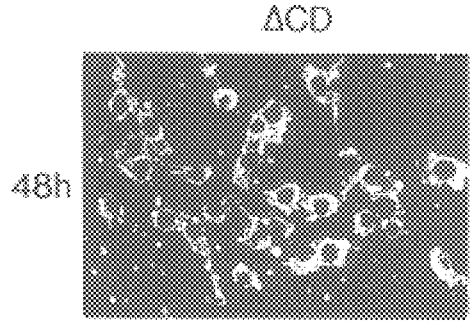

Recombinant RV (SAD DCD) was recovered as described in Example 1. As expected, a truncated G protein was expressed in cells infected with SAD DCD (FIG. 10). Compared to standard sequence virus SAD L16, 100 fold lower titres were obtained with SAD DCD virus after infection of cells at an m.o.i. of 1. In addition, a reduced rate of spread in cell cultures was observed (FIG. 11), indicating that the truncation of the G protein resulted in reduced assembly of virions or reduced cell infectivity of virions. To analyse the behaviour of SAD DCD in infected animals, five mice were injected intracerebrally with $10^5$ ffu of SAD DCD and 5 mice with the same dosis of SAD L16.

EXAMPLE 7
Generation of a Rabies Virus G-minus (G⁻) Mutant by Complementation in Trans In order to delete the entire G protein coding region from the RV genome, the full length clone pSAD UE (Example 2) was used. This clone differs from pSAD L16 by the presence of a unique NheI site within the nontranslated 3' region of the G gene (SAD B19 position 5339). By partial digestion of pSAD U2 with PflMI (SAD position 3176) and complete digestion with NheI, subsequent fill-in by Klenow enzyme and religation, a cDNA fragment comprising SAD B19 nucleotides 3177–5339 was removed. The resulting clone pSAD dG was used in transfection experiments to recover recombinant virus. In addition to plasmids encoding N, P, and L proteins, however, a plasmid encoding the G protein was cotransfected with pSAD dG to complement the G deficiency of the viral genome. The resulting virus SAD dG was passaged to cells again transfected with the G encoding plasmid and infected with the vaccinia virus vTF-7-3 to provide G protein.

Figures 12A, 12B:
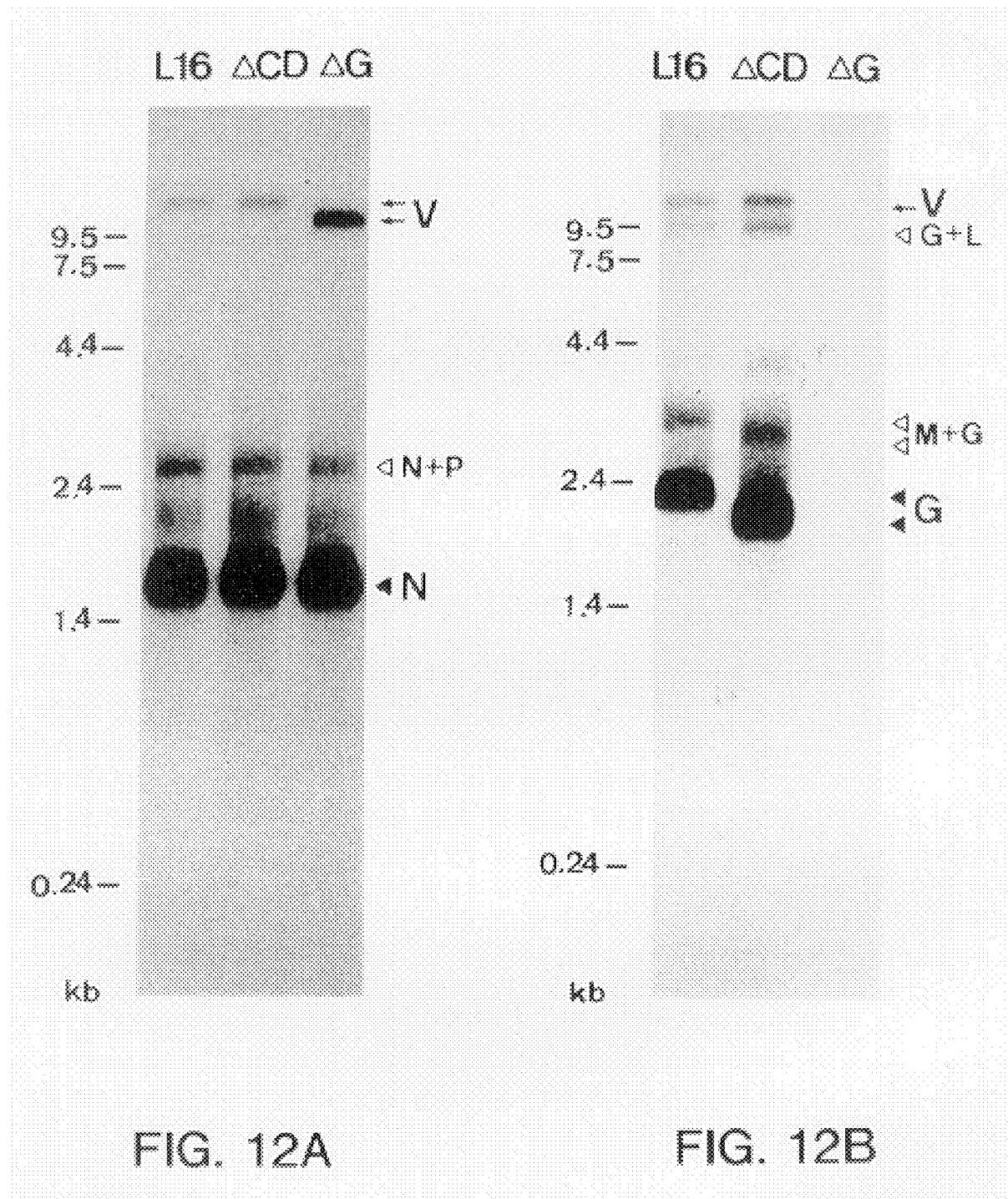

RNA transcripts of SAD dG were analyzed by Northern blotting experiments. After hybridization with an N specific probe, the SAD dG genome was found to be considerably smaller than the rabies virus wt genome reflecting the cDNA deletion of 2.1 kb. A probe spanning the entire G coding region, however, failed to hybridize with SAD dG RNAs demonstrating the lack of G encoding sequences (FIG. 12). The identity of the deletion was further confirmed by RT-PCR and sequencing.

Figure 13A:
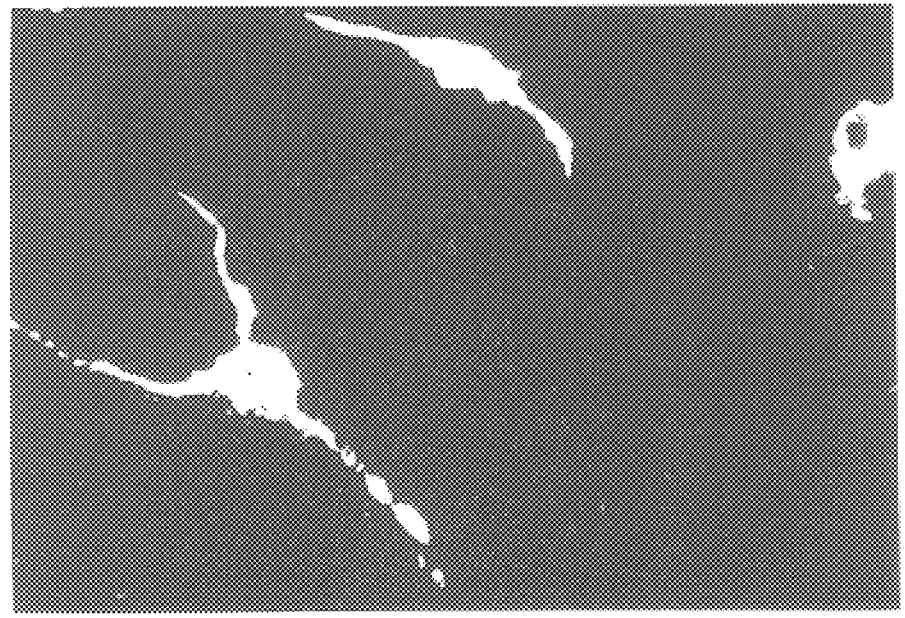
Figure 13B:
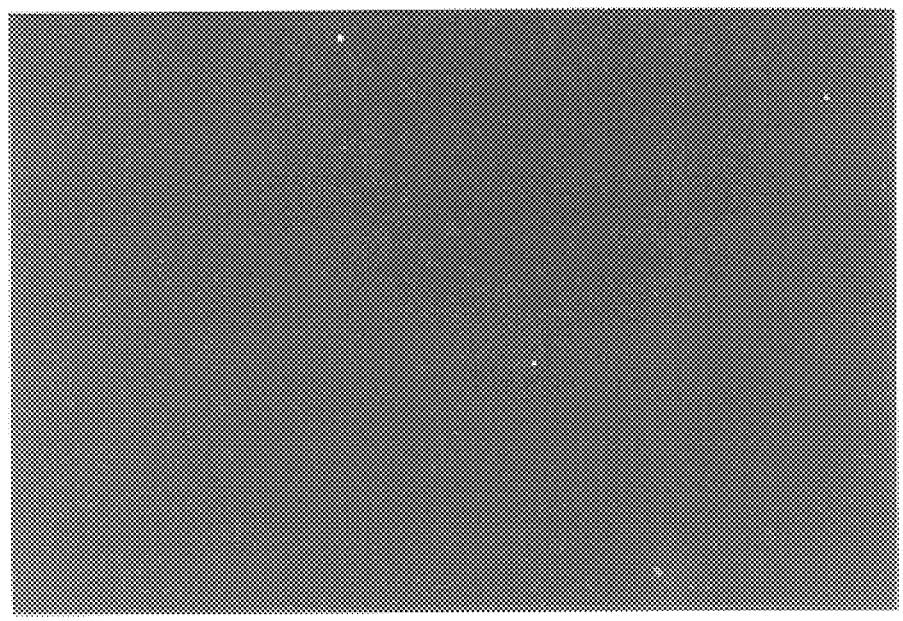

Phenotypically complemented SAD dG was able to infect noncomplementing BSR cells, to replicate its genome and to express the genes encoded by the genome. However, it was not able to produce infectious virions and thus, infection could not spread to other cells (FIG. 13) or be transferred by passage of culture supernatants to other cell cultures.

EXAMPLE 8
Complementation of G Mutants by Heterologous Glycoproteins: Directing Virus to Specific Cells To demonstrate that heterologous surface proteins may be incorporated functionally in the envelope of a recombinant virus, the G-mutant SAD dG was complemented by recombinant viral glycoproteins as described in Example 7 for the rabies virus G. Infectious pseudotype particles were generated that contained the spike proteins from Mokola virus, another member of the Lyssavirus genus, the rhabdovirus vesicular stomatitis virus (VSV; serotype New Jersey, genus vesiculovirus) and from the retrovirus human immunodeficiency virus (HIV-1, strain NL-43).

Expression from transfected plasmids of the authentic Mokola and VSV-G protein and infection of cells with SADdG resulted in the formation of infectious pseudotype viruses. Compared to rabies virus G and the closely related Mokola virus G, however, a reduced titre was observed with VSV-G ($10^4$/ml in contrast to $10^6$/ml). After replacement of the cytoplasmic and transmembrane domain sequence of VSV-G by the corresponding domains of the rabies virus G protein, however, $10^6$ infectious particles were generated suggesting that the cytoplasmic domain of the RV G is directing the protein into the viral envelope.

The generation of pseudotype particles containing authentic HIV gp160 (gp 120/40) spikes was not observed. In contrast, expression of a chimeric protein composed of the ecto- and transmembrane domain of the HIV gp fused to the cytoplasmic domain of RV G resulted in the formation of RV(HIV) pseudotypes. This confirmed that the cytoplasmic domain of the G protein is responsible for efficient incorporation of spike proteins into the envelope of rhabdoviruses. The RV(HIV) pseudotype particles successfully infected Vero cells expressing the human CD4 surface protein ($T4^+$ cells) but not the control cells expressing CD8 ($T8^+$ cells) (cells were obtained from the AIDS Research and Reference Reagent Programme). The pseudotype viruses thus possess the host range and cell specificity of HIV.

BRIEF DESCRIPTION OF THE DRAWINGS

FIG. 1:

Organization of the RV pseudogene region (ψ) and construction of recombinant RV genomes (drawn to scale). Numbers indicate the nucleotide positions in the antigenome sequence of SAD B19. On top, the entire RV genome with its five open reading frames is shown. Mutations were carried out in pPsiX8 containing part of the genome (3823–6668) and reintroduced into the full length clone pSAD L16 by exchange of the StuI fragment (4014–6364). In the detail drawing, coding regions are represented by gray boxes, non-coding sequences as lines. Functional transcriptional signal sequences are indicated by filled bar (stop/polyadenylation) and arrowhead (mRNA transcription start). The non-functional signal-like sequence defining the start of the ψ region is shown by the open bar. Arrows indicate the position of oligonucleotide primers G3P and L4M used for RT-PCR analysis of the ψ region. In SAD U2, fill-in of HindIII extensions resulted in insertion of 4 nucleotides and generation of a unique NheI-site. In SAD V*, a cDNA fragment containing the RV N/P cistron border (SAD B19 nucleotides 1323–1502) was inserted into the StyI site; SAD W9 possesses a deletion of the StyI/HindIII fragment.

FIG. 2:

Simplified scheme for the construction of transcription plasmids containing full length RV cDNA. Numbers refer to nucleotide positions of the SAD B19 RV antigenome sequence (Conzelmann et al., 1990). The plasmid pSDI-1plus which served as a basis for reconstruction of full length RV genomic DNA is a counterpart of pSDI-1 (Conzelmann and Schnell, 1994) containing the SDI-1 RV mini-genome that comprises the terminal nucleotides 1–68 and 11760–11928 in opposite direction with respect to T7 RNA polymerase promoter (T7) and hepatitis delta virus antigenomic ribozyme sequence (HDV). The MunI-BglII fragment of pSDI-1 plus was replaced with a 1 kb cDNA construct that was assembled from three SAD B19 cDNA clones as indicated. Insertion of a 3.6 kb SphI and a 7.2 kb AatII fragment which were assembled from two cDNA clones each resulted in the final plasmid pSAD L16 containing full length SAD B19 cDNA. Transcription of this plasmid by T7 RNA polymerase should yield positive stranded (antigenomic) RNA possessing three extra non-viral G residues at the 5' and a precise 3' end after autolysis of the ribozyme. (T7) T7 promoter; (T7T) T7 transcription terminator; (HDV) HDV antigenomic ribozyme sequence.

FIG. 3:

Demonstration of the genetic tag in the genome of the transfectant virus SAD U2.

Total RNA from cells infected with standard RV SAD B19 (B19) and transfectant viruses SAD L16 (L16) and SAD U2 (U2) was isolated 2 days post infection and used for RT-PCR amplification of the respective ψ regions with primers G3P and L4M. The amplified DNA was separated in a 1% agarose gel directly and after digestion with HindIII and NheI, respectively. A NheI restriction site is present only in DNA derived from SAD U2.M,DNA size marker.

FIG. 4:

PCR analysis of SAD B19 (B19), SAD V* (V*), and SAD W9 (W9) genomes. RT-PCR was performed as described in FIG. 3 with primers G3P and L4M. Amplification products were separated in a 1% agarose gel.

FIG. 5:

Demonstration of CAT mRNAs transcribed by recombinant RVS.

A Northern blot of total RNA from cells infected with SAD L16 (L16), SAD XCAT (X6) and SAD VCAT (VC 18), was hybridized with probes specific for the G gene (G), pseudogene-(Y), and CAT gene, respectively. On the left side the viral genomes (v) and particular mRNAs are indicated. While SAD XCAT transcribes an mRNA containing both CAT and pseudogene sequences ("CATY"), SAD VCAT lacks pseudogene sequences and transcribes an mRNA ("CAT") possessing only CAT sequences. The size of RNA markers are given in kb.

FIG. 6:

CAT activity of SAD XCAT and SAD VCAT after multiple passages in cell culture. Cells were infected with viruses from the particular passages (number of passage as indicated) and equal amounts of cell extracts were analysed for CAT activity two days post infection. In lane "–" extracts from cells infected with SAD L16 were analysed.

FIG. 7:

Expression of E0 and E2 protein by recombinant RVs.

Cells were infected with SAD VE0 (isolates 1, 2, 3) and SAD VE2 (isolates a, b, c), respectively. Two days post infection, cell extracts were separated in PAA Gels under reducing conditions and transferred to nitrocellulose membranes. After incubation with monoclonal antibodies directed against CSFV E0 and E2 protein, respectively, and subsequently with a secondary antibody coupled to alkaline phosphatase, the proteins were visualized by addition of substrate and exposure to an X-ray film. As a control, baculovirus expressed and purified E0 and E2 protein was used (B). In addition, extracts from cells infected with CSFV (V) served for comparison.

FIG. 8:

Leucocytes of pigs immunized with SAD VE0 (#1 and 2), SAD VE2 (#6) and standard rabies virus SAD B19 (#3 and #4), and challenged with CSVF. Leucocyte amounts are given in percent of absolute numbers present prior to challenge (day 0). * (#1, day 10 p.ch.): not done, estimated value.

FIG. 9A:

Body temperature of pigs after CSFV challenge (day 0).

Animals immunized with SAD VE0 (#1 and #2) developed mild fever until day 11 (#1) or no fever (#2). Both control animals immunized with SAD B19 (#3 and #4) showed high fever over a long period. #4 died at day 15 post challenge from classical swine fever, due to heavy symptoms, #4 was killed 21 days post challenge.

FIG. 9B:

The animal immunized with SAD VE2 developed mild fever only at days 6 to 8. Controls are the same as in FIG. 9A.

FIG. 10:

Expression of a truncated G protein in cells infected with SAD DCD. BSR cells were infected at an moi of 1 with SAD DCD or SAD L16 and at 16 h post-infection labelled with 50 µCi of [$^{35}$S]methionine for 3 h. Cell extracts were incubated with an anti-rabies G MAb and aliquots of immunoprecipitated samples were either digested with PNGase F (+PF) in order to demonstrate the protein backbones or mock treated (–) to demonstrate the glycosylated proteins. +TM: infected cells were incubated in the presence of 2 µg/ml tunicamycin for 90 min prior to labelling and during the 3 h labelling period. Proteins were separated on 10% SDS-PAGE and visualized by autoradiography. Cell extracts were analysed as above. L16, SAD L16 virus; ΔCD, SAD DCD mutant virus. M: Protein size markers.

FIG. 11:

Spread of SAD L16 and SAD DCD in cell culture. Culture cells were infected at an m.o.i. of 0.05 with SAD L16 (L16) and SAD DCD (DCD), respectively, and analysed at the indicated times post infection by direct immunofluorescence with a conjugate (Centocor®) directed against rabies virus N protein. A slower spread of infection of neighbouring cells is observed in cells infected with SAD DCD.

FIG. 12:

Analysis of SAD dG (Example 7) and SAD dCD (Example 6) specific RNA's. Total RNA of BSR cells infected with SAD L16 (Example 1), SAD dCD (ΔCD) and phenotypically complemented SAD dG virus (ΔG) at m.o.i.s. of 1 was isolated 2 days post infection and analyzed by Northern hybridization. As demonstrated by hybridization with an N gene specific probe (A), the genome of SAD dG is considerably smaller than the standard rabies virus genome (v), reflecting the 2.1 kb deletion of the G gene. A probe spanning the entire G protein encoding sequence fails to hybridize with SAD dG RNAs. The small deletion of the cytoplasmic domain encoding region in the SAD dCD genome is demonstrated by the appearance of a G mRNA (G) that is shorter than the standard rabies virus G mRNA.

v: genomic RNA; N, G: monocistronic mRNAs; N+P, M+G, G+L: bicistronic mRNAs

FIG. 13:

Lack of spread of the G⁻ mutant SAD dG. BSR cells were infected with phenotypically complemented SAD dG and analyzed 36 hours post transfection by immunofluorescence microscopy. In (A) N protein expression is shown by incubation of cells with a FITC-coupled antibody directed against N protein (Centocore). Only single cells are infected, no spread of virus to neighbouring cells is observed. (B): control with a G specific antibody.

FIG. 14:

Composition of the functional chimeric HIV/RV glycoprotein used for generation of RV(HIV) pseudotype virions. The entire HIV-NL43 gp160 cytoplasmic domain except for three amino acids directly downstream of the transmembrane domain was replaced by the complete RV-G cytoplasmic domain. "p" represents a proline residue not present in the parental proteins. Cytoplasmic and transmembrane domain sequences are separated by a slash (/).

---

I claim:

1. A genetically manipulated, infectious, replicating, non-segmented negative-stranded RNA virus mutant, comprising at least one alteration selected from an insertion and a deletion, wherein the alteration is in a region of the virus genome selected from an open reading frame, a pseudogene region and an intergenic region.

2. The virus mutant according to claim 1, comprising at least one alteration selected from an insertion and a deletion, wherein the alteration is in a pseudogene region.

3. The virus mutant according to claim 1, comprising at least one alteration selected from an insertion and a deletion, wherein the alteration is in an open reading frame.

4. The virus mutant according to claim 3, comprising at least one alteration in the open reading frame encoding the Matrix protein or an analog thereof, resulting in the absence of a functional Matrix protein, wherein said mutant can be grown when phenotypically complemented with a functional Matrix protein.

5. The virus mutant according to claim 3, comprising at least one alteration selected from an insertion and a deletion, wherein the alteration is in the open reading frame encoding the glycoprotein G.

6. The virus mutant according to claim 5, wherein the alteration results in the absence of a functional glycoprotein G, wherein said mutant can be grown when phenotypically complemented with a functional glycoprotein G analog.

7. The virus mutant according to claim 6, wherein the glycoprotein G analog is the rabies glycoprotein G.

8. The virus mutant according to claim 1, comprising a heterologous nucleic acid sequence encoding an epitope or polypeptide of a pathogenic virus or microorganism.

9. The virus mutant according to claim 1, wherein the virus mutant belongs to the family of paramyxoviridae.

10. The virus mutant according to claim 1, wherein the virus mutant belongs to the family of rhabdoviridae.

11. The virus mutant according to claim 10, wherein the virus mutant is a rabies virus.

12. A vaccine for the prevention of infection caused by a non-segmented negative-stranded RNA virus in a mammal, comprising a virus mutant according to claim 1 and a pharmaceutically acceptable carrier or diluent.

13. A process for the preparation of an infectious, replicating, non-segmented, negative-stranded RNA virus comprising the steps of:

a) providing a host cell expressing a heterologous RNA polymerase;

b) introducing into said host cell
   1) one or more DNA molecules encoding the virus N, P and L proteins, or analogs thereof operably linked to expression control sequence functional in said host cell; and
   2) a DNA molecule comprising the cDNA of the non-segmented negative-stranded RNA virus wherein the cDNA encodes the entire genome of the virus or is modified by the incorporation of a mutation, and wherein the DNA molecule is transcribed by the heterologous RNA polymerase, and c) isolating the viruses produced by the cells.

14. The process according to claim 13, wherein the cDNA of the non-segmented negative-stranded RNA virus genome is modified by the incorporation of a mutation.

15. The process according to claim 13, wherein the transcripts of the non-segmented negative-stranded RNA virus cDNA genome are positive stranded antigenomic RNAs.

16. The process according to claim 13, wherein the RNA polymerase is T7 RNA polymerase.

17. The process according to claim 13, wherein the non-segmented negative-stranded RNA virus genome is obtained from the family of paramyxoviridae.

18. The process according to claim 13, wherein the non-segmented negative-stranded RNA virus genome is obtained from the family of rhabdoviridae.

19. The process according to claim 18, wherein the non-segmented negative-stranded RNA virus genome is obtained from the rabies virus.

* * * * *